US008423384B2

United States Patent
Hertel et al.

(10) Patent No.: US 8,423,384 B2
(45) Date of Patent: *Apr. 16, 2013

(54) PROVIDING MULTIDISCIPLINARY ACTIVITIES IN CONTEXT OF CLINICIAN'S ROLE RELEVANT ACTIVITIES

(75) Inventors: Cheryl Hertel, Blue Springs, MO (US); Eva Karp, Kansas City, MO (US)

(73) Assignee: Cerner Innovation, Inc., Overland Park, KS (US)

( * ) Notice: Subject to any disclaimer, the term of this patent is extended or adjusted under 35 U.S.C. 154(b) by 653 days.

This patent is subject to a terminal disclaimer.

(21) Appl. No.: 11/777,547

(22) Filed: Jul. 13, 2007

(65) Prior Publication Data

US 2008/0086330 A1 Apr. 10, 2008

Related U.S. Application Data

(60) Provisional application No. 60/828,531, filed on Oct. 6, 2006.

(51) Int. Cl.
*G06Q 10/00* (2006.01)
(52) U.S. Cl.
USPC .................................................. 705/3; 705/2
(58) Field of Classification Search .................. 705/2, 3
See application file for complete search history.

(56) References Cited

U.S. PATENT DOCUMENTS

| | | | |
|---|---|---|---|
| 5,583,758 A | 12/1996 | McIlroy et al. | |
| 5,772,585 A | 6/1998 | Lavin et al. | |
| 5,781,442 A | 7/1998 | Engleson et al. | |
| 5,855,006 A | 12/1998 | Huemoeller et al. | |
| 5,953,704 A | 9/1999 | McIlroy et al. | |
| 5,970,466 A | 10/1999 | Detjen et al. | |
| 6,047,259 A | 4/2000 | Campbell et al. | |
| 6,108,665 A | 8/2000 | Bair et al. | |
| 6,957,187 B1 | 10/2005 | Kameda | |
| 7,512,541 B2 | 3/2009 | Stroup et al. | |
| 7,542,911 B2 * | 6/2009 | Barret et al. | 705/2 |
| 7,587,329 B2 | 9/2009 | Thompson et al. | |
| 2003/0046114 A1 | 3/2003 | Davies et al. | |
| 2003/0050801 A1 | 3/2003 | Ries et al. | |

(Continued)

OTHER PUBLICATIONS

Non Final Office Action for U.S. Appl. No. 11/777,544 mailed Jan. 28, 2010.

(Continued)

*Primary Examiner* — Robert Morgan
*Assistant Examiner* — Maroun Kanaan
(74) *Attorney, Agent, or Firm* — Shook, Hardy & Bacon LLP

(57) ABSTRACT

Management of patient activities for a clinician is provided by a patient activity list the may present the clinician's role relevant activities in conjunction with multidisciplinary activities to be performed for a patient. A timeline view area is presented having role relevant scheduled activities for one or more patients assigned to the clinician. Each role relevant scheduled activity comprises an activity to be performed by the clinician and is presented in the timeline view area based on a scheduled time and in association with a corresponding patient. When a user selection of at least one of the patients is received, one or more multidisciplinary activities for the patient are presented within the timeline view area. The multidisciplinary activities include activities scheduled to be performed by other clinicians, and each multidisciplinary activity is presented in the timeline view area based on a scheduled time.

13 Claims, 24 Drawing Sheets

U.S. PATENT DOCUMENTS

| | | |
|---|---|---|
| 2003/0135388 A1 | 7/2003 | Martucci et al. |
| 2003/0140928 A1 | 7/2003 | Bui et al. |
| 2003/0140929 A1 | 7/2003 | Wilkes et al. |
| 2003/0233253 A1 | 12/2003 | Peth et al. |
| 2003/0236683 A1 | 12/2003 | Henderson et al. |
| 2004/0010425 A1 | 1/2004 | Wilkes et al. |
| 2004/0078231 A1 | 4/2004 | Wilkes et al. |
| 2004/0143459 A1 | 7/2004 | Engleson et al. |
| 2004/0172299 A1 | 9/2004 | Paul |
| 2004/0215499 A1 | 10/2004 | Leist |
| 2005/0114283 A1 | 5/2005 | Pearson et al. |
| 2005/0154613 A1 | 7/2005 | Kade |
| 2005/0215867 A1 | 9/2005 | Grigsby et al. |
| 2006/0053044 A1 | 3/2006 | Kurian et al. |
| 2006/0085223 A1* | 4/2006 | Anderson et al. ............ 705/2 |
| 2006/0271399 A1 | 11/2006 | Robson et al. |
| 2006/0287885 A1 | 12/2006 | Frick |
| 2006/0293920 A1* | 12/2006 | Stroup et al. ............ 705/2 |
| 2007/0094045 A1 | 4/2007 | Cobbs et al. |
| 2007/0094046 A1* | 4/2007 | Cobbs et al. ............ 705/2 |
| 2007/0100660 A1 | 5/2007 | Carosso et al. |
| 2007/0203755 A1 | 8/2007 | Wilson et al. |
| 2007/0255586 A1 | 11/2007 | Green et al. |
| 2007/0265882 A1 | 11/2007 | Jennings et al. |

OTHER PUBLICATIONS

Non Final Office Action for U.S. Appl. No. 11/777,540 mailed Jan. 21, 2010.
Non Final Office Action for U.S. Appl. No. 11/777,573 mailed Mar. 31, 2010.
Non Final Office Action for U.S. Appl. No. 11/777,584 mailed Mar. 25, 2010.
Non-Final Office Action for U.S. Appl. No. 11/777,561 mailed May 12, 2010, 16 pages.
Non-Final Office Action for U.S. Appl. No. 11/777,579 mailed May 24, 2010, 15 pages.
Non-Final Office Action mailed Jun. 22, 2010, 19 pages, regarding U.S. Appl. No. 11/777,589.
Non-Final Office Action mailed Jun. 22, 2010, 11 pages, regarding U.S. Appl. No. 11/777,569.
Final Office Action mailed Jul. 8, 2010, 15 pages, regarding U.S. Appl. No. 11/777,540.
Final Office Action mailed Jul. 6, 2010, 18 pages, regarding U.S. Appl. No. 11/777,544.
Final Office Action mailed Sep. 14, 2010 regarding U.S. Appl. No. 11/777,584, 22 pages.
Final Office Action mailed Oct. 1, 2010 regarding U.S. Appl. No. 11/777,579, 19 pages.
Final Office Action mailed Oct. 14, 2010 regarding U.S. Appl. No. 11/777,573, 30 pages.
Final Office Action mailed Oct. 25, 2010 regarding U.S. Appl. No. 11/777,569, 21 pages.
Non-Final Office Action mailed Oct. 26, 2010 regarding U.S. Appl. No. 11/777,544, 19 pages.
Final Office Action mailed Oct. 26, 2010 regarding U.S. Appl. No. 11/777,561, 14 pages.
Non-Final Office Action mailed Nov. 24, 2010 regarding U.S. Appl. No. 11/777,540, 16 pages.
Non-Final Office Action mailed Mar. 3, 2011 regarding U.S. Appl. No. 11/777,584 18 pages.
Final Office Action mailed Jan. 19, 2011 regarding U.S. Appl. No. 11/777,589 25 pages.
Non-Final Office Action mailed Nov. 24, 2010 regarding U.S. Appl. No. 11/777,540 16 pages.
Non-Final Office Action mailed Mar. 30, 2011 regarding U.S. Appl. No. 11/777,573 28 pages.
Final Office Action mailed Apr. 5, 2011 regarding U.S. Appl. No. 11/777,544 22 pages.
Non-Final Office Action mailed Apr. 13, 2011 regarding U.S. Appl. No. 11/777,569 17 pages.
Final Office Action mailed May 11, 2011 regarding U.S. Appl. No. 11/777,540 16 pages.
Non-Final Office Action mailed Oct. 1, 2012 regarding U.S. Appl. No. 11/777,573 25 pages.
Notice of Allowance mailed Sep. 20, 2012 regarding U.S. Appl. No. 11/777,540 86 pages.
Non-Final Office Action mailed Sep. 21, 2012 regarding U.S. Appl. No. 11/777,579 17 pages.
Final Office Action mailed Sep. 6, 2011 regarding U.S. Appl. No. 11/777,584 16 pages.
Final Office Action mailed Dec. 5, 2011 regarding U.S. Appl. No. 11/777,573 27 pages.
Non-Final Office Action mailed Nov. 2, 2012 regarding U.S. Appl. No. 11/777,561 40 pages.

* cited by examiner

PROVIDING MULTIDISCIPLINARY ACTIVITIES IN CONTEXT OF CLINICIAN'S ROLE RELEVANT ACTIVITIES

CROSS-REFERENCE TO RELATED APPLICATIONS

This application claims the benefit of U.S. Provisional Application No. 60/828,531 filed Oct. 6, 2006. Additionally, this application is related by subject matter to the invention disclosed in the following U.S. patent applications filed on even date herewith: U.S. application Ser. No. 11/777,540, entitled "Patient Activity Coordinator;" U.S. application Ser. No. 11/777,589, entitled "Providing Clinical Activity Details in Context;" U.S. application Ser. No.11/777,544, entitled "Rescheduling Clinical Activities in Context of Activities View;" U.S. application Ser. No. 11/777,573, entitled "Viewing Clinical Activity Details within a Selected Time Period;" U.S. application Ser. No. 11/777,584, entitled "Documentation of Medication Activities in Context of MAR;" U.S. application Ser. No. (not yet assigned) 11/777,561, entitled "Acknowledgement of Previous Results for Medication Administration;" U.S. application Ser. No. 11/777,569, entitled "Clinical Activity Navigator;" U.S. application Ser. No. 11/777,579, entitled "Patient Outcomes in Context of Documentation;" each of which is assigned or under obligation of assignment to the same entity as this application, and incorporated in this application by reference.

STATEMENT REGARDING FEDERALLY SPONSORED RESEARCH OR DEVELOPMENT

Not applicable.

BACKGROUND

Clinicians in many healthcare organizations are more frequently being tasked to treat a greater number of patients. Additionally, clinicians must often perform a wide variety of care-related activities for each of their patients. These activities are typically based on a clinician's role. For example, activities for a nurse may include administering medications, performing patient assessments, collecting specimens from patients, and providing general patient care. Given the increased number of patients that clinicians are treating, it is often difficult for clinicians to manage the various activities associated with each of their patients. This increased case load and the accompanying stress can result in a greater number of medical errors.

A variety of computer-based solutions have been developed to assist clinicians in the care of patients. Such solutions provide clinicians with access to patient information and allow clinicians to manage patient activities. However, many of these solutions have not been well constructed. In particular, some solutions present too much information to the clinician, forcing the clinician to sift through the data to find desired information. This can be a time-consuming process for clinicians. As a result, many clinicians resort to a manual process of recording the most vital patient information, for example, on a note card that they carry around with them.

In some cases, current computer-based solutions require clinicians to move between various different applications to find patient information, view activities, and document completion of activities. As such, clinicians typically cannot maintain a context of the activities they need to perform during a particular shift. Further, if clinicians are interrupted while performing a workflow using a current solution, the clinician typically must start the workflow from the beginning when returning to complete the workflow.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present invention relate to facilitating clinicians in the management of patient activities. A patient activity list may be provided with a common view that allows a clinician to review assigned patients and activities for a work period. The patient activity list limits the amount of information presented but is fully navigable to allow the clinician to access further information and complete activities within context of the clinician's activities. Additionally, an activities navigator manages the completion of activities selected by a clinician.

Accordingly, in one aspect, an embodiment of the invention is directed to a method in a clinical computing environment for facilitating management of activities for a clinician. The method includes presenting a timeline view area having role relevant scheduled activities for one or more patients assigned to the clinician, each role relevant scheduled activity comprising an activity to be performed by the clinician and being presented in the timeline view area based on a scheduled time and in association with a corresponding patient. The method also includes receiving a user selection of at least one of the patients. The method further includes presenting one or more multidisciplinary activities for the selected patient within the timeline view area, the one or more multidisciplinary activities comprising activities scheduled to be performed by one or more other clinicians, each multidisciplinary activity being presented in the timeline view area based on a scheduled time.

In another embodiment, an aspect of the invention is directed to one or more computer-readable media having computer-useable instructions embodied thereon for presenting a graphical user interface for facilitating the management of activities for a clinician. The graphical user interface includes a timeline view area presenting role relevant scheduled activities for one or more patients assigned to the clinician, each role relevant scheduled activity comprising an activity to be performed by the clinician and being presented in the timeline view area based on a scheduled time and in association with a corresponding patient. The timeline view area also presents one or more multidisciplinary activities for at least one patient within the timeline view area, the one or more multidisciplinary activities comprising activities scheduled to be performed by one or more other clinicians, each multidisciplinary activity being presented in the timeline view area based on a scheduled time.

A further embodiment of the invention is directed to a method in a clinical computing environment for facilitating management of activities for a clinician. The method includes presenting a timeline view area having role relevant scheduled activities for one or more patients assigned to the clinician, each role relevant scheduled activity comprising an activity to be performed by the clinician and being presented in the timeline view area based on a scheduled time and in association with a corresponding patient. The method also includes presenting one or more multidisciplinary activities for at least one patient within the timeline view area, the one or more multidisciplinary activities comprising activities scheduled to be performed by one or more other clinicians, each multidisciplinary activity being presented in the timeline view area based on a scheduled time.

BRIEF DESCRIPTION OF THE SEVERAL VIEWS OF THE DRAWINGS

The present invention is described in detail below with reference to the attached drawing figures, wherein:

FIG. 2 is an illustrative screen display showing an exemplary patient activity list in accordance with an embodiment of the present invention;

FIG. 3 is an illustrative screen display showing an exemplary patient activity list with a critical indicators window in accordance with an embodiment of the present invention;

FIG. 4 is an illustrative screen display showing an exemplary patient activity list with a patient snapshot in accordance with an embodiment of the present invention;

Figure 5:
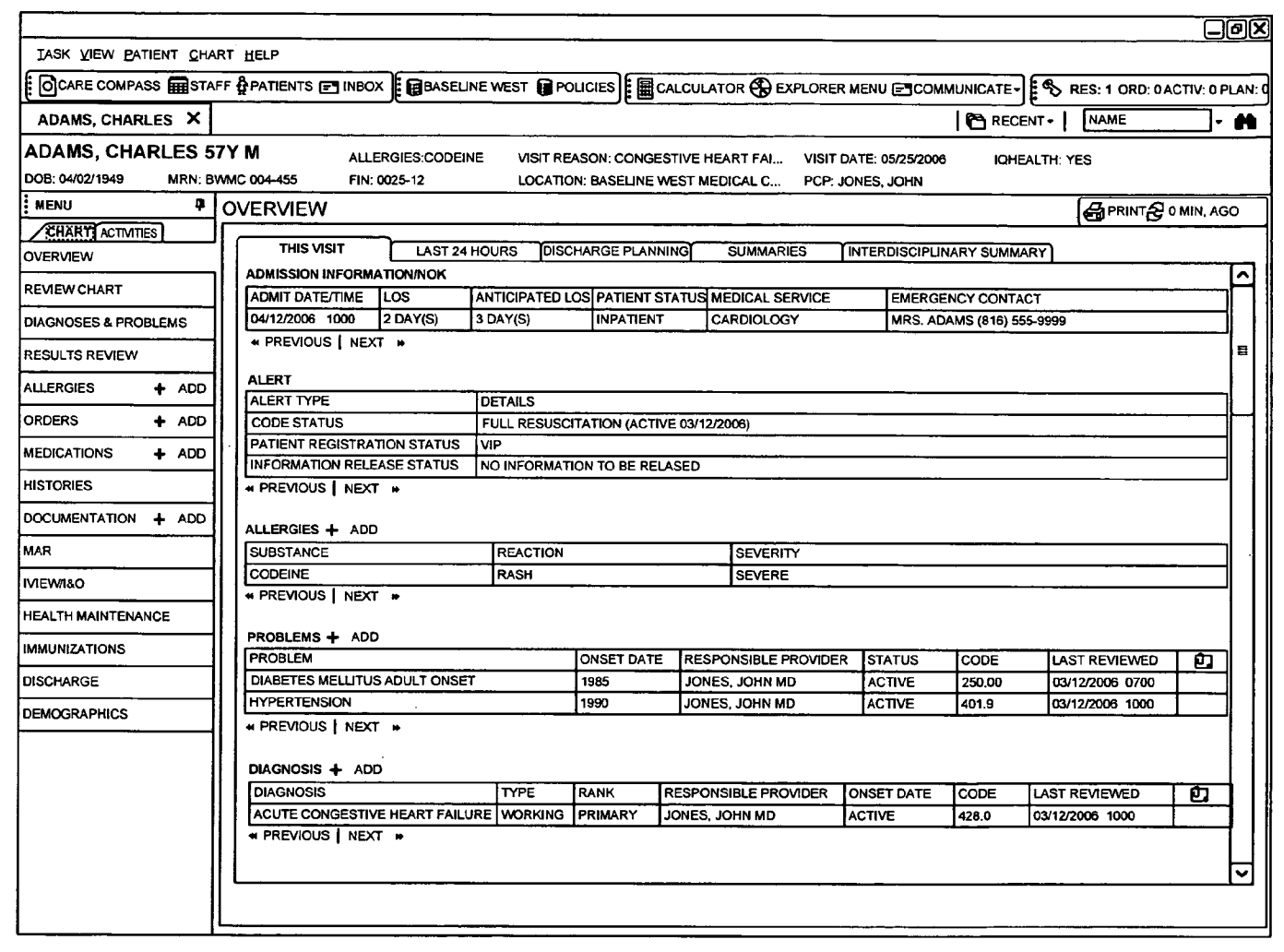

FIG. 5 is an illustrative screen display showing a patient chart accessed from a patient activity list in accordance with an embodiment of the present invention;

FIG. 7 is an illustrative screen display showing critical results associated with a key notification in accordance with an embodiment of the present invention;

FIG. 8 is an illustrative screen display showing an exemplary patient activity list with an action pane including details to selected activities in accordance with an embodiment of the present invention;

FIG. 9 is an illustrative screen display showing rescheduling of an activity in a patient activity list in accordance with an embodiment of the present invention;

FIG. 10 is an illustrative screen display showing the result of rescheduling of an activity in a patient activity list in accordance with an embodiment of the present invention;

FIG. 11 is an illustrative screen display showing a patient activity list in a column view in accordance with an embodiment of the present invention;

Figure 12:
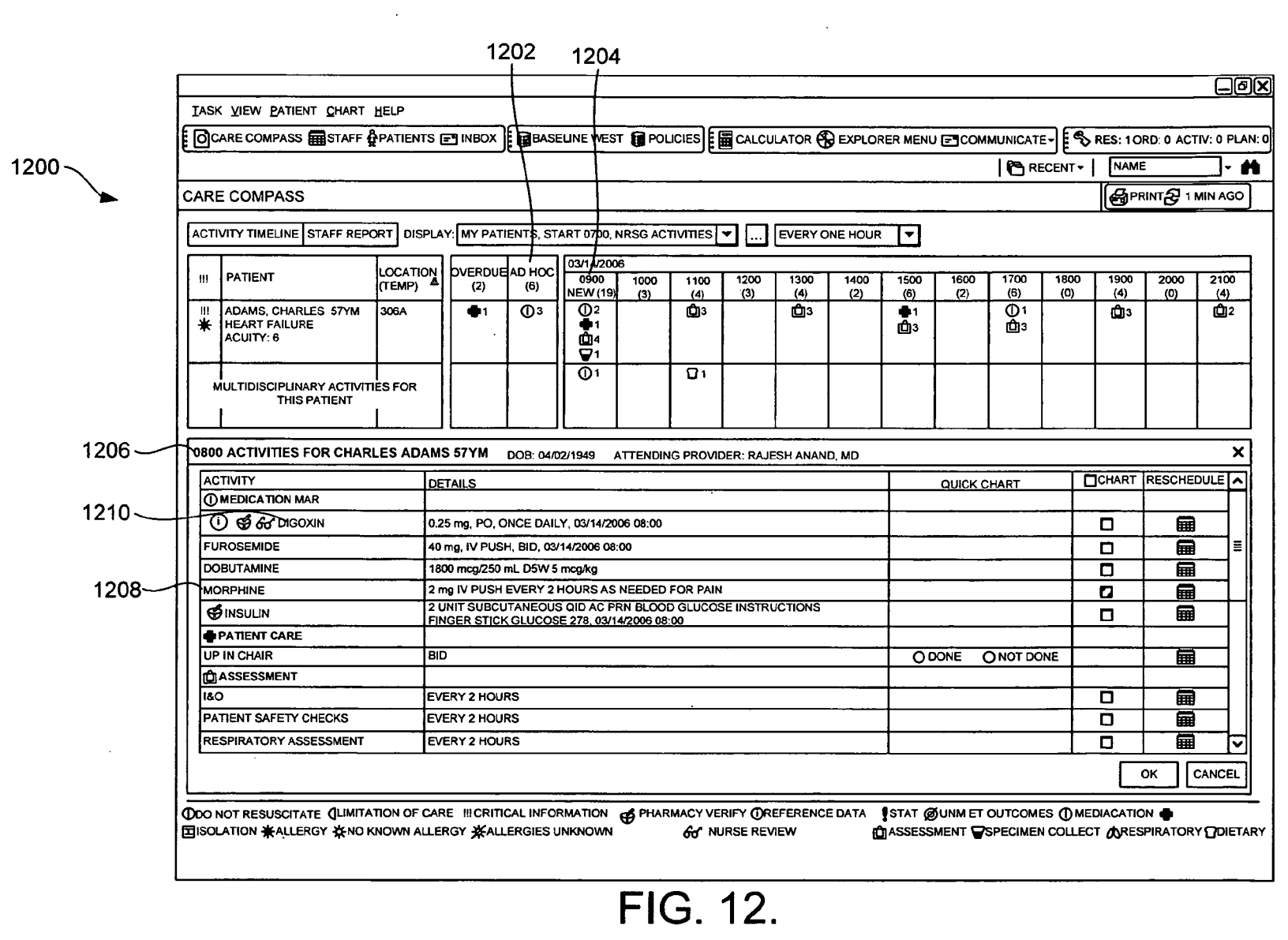

FIG. 12 is an illustrative screen display showing an action pane having activities from multiple cells selected in a patient activity list in accordance with an embodiment of the present invention;

FIG. 13 is an illustrative screen display including a window showing details of an activity selected within a patient activity list in accordance with an embodiment of the present invention;

FIG. 14 is an illustrative screen display including a window showing details of another activity selected with a patient activity list in accordance with an embodiment of the present invention;

FIG. 15 is an illustrative screen display showing the selection of activities for charting in accordance with an embodiment of the present invention;

FIG. 16 is an illustrative screen display showing a medication administration record accessed from a patient activity list in accordance with an embodiment of the present invention;

FIG. 17 is an illustrative screen display showing the documentation of an activity in a medication administration record accessed from a patient activity list in accordance with an embodiment of the present invention;

FIG. 18 is an illustrative screen display showing the acknowledgement of a related result provided in a medication administration record in accordance with an embodiment of the present invention;

FIG. 19 is an illustrative screen display showing a full view medication administration record in accordance with an embodiment of the present invention;

FIG. 20 is an illustrative screen display showing an activity navigator in accordance with an embodiment of the present invention;

FIG. 21 is an illustrative screen display showing assessment documentation with outcome icons in accordance with an embodiment of the present invention;

FIG. 22 is an illustrative screen display showing an outcome window in accordance with an embodiment of the present invention;

FIG. 23 is an illustrative screen display showing completion of assessment documentation in accordance with an embodiment of the present invention; and FIG. 24 is an illustrative screen display showing an outcome summary in accordance with an embodiment of the present invention.

DETAILED DESCRIPTION

Figure 1:
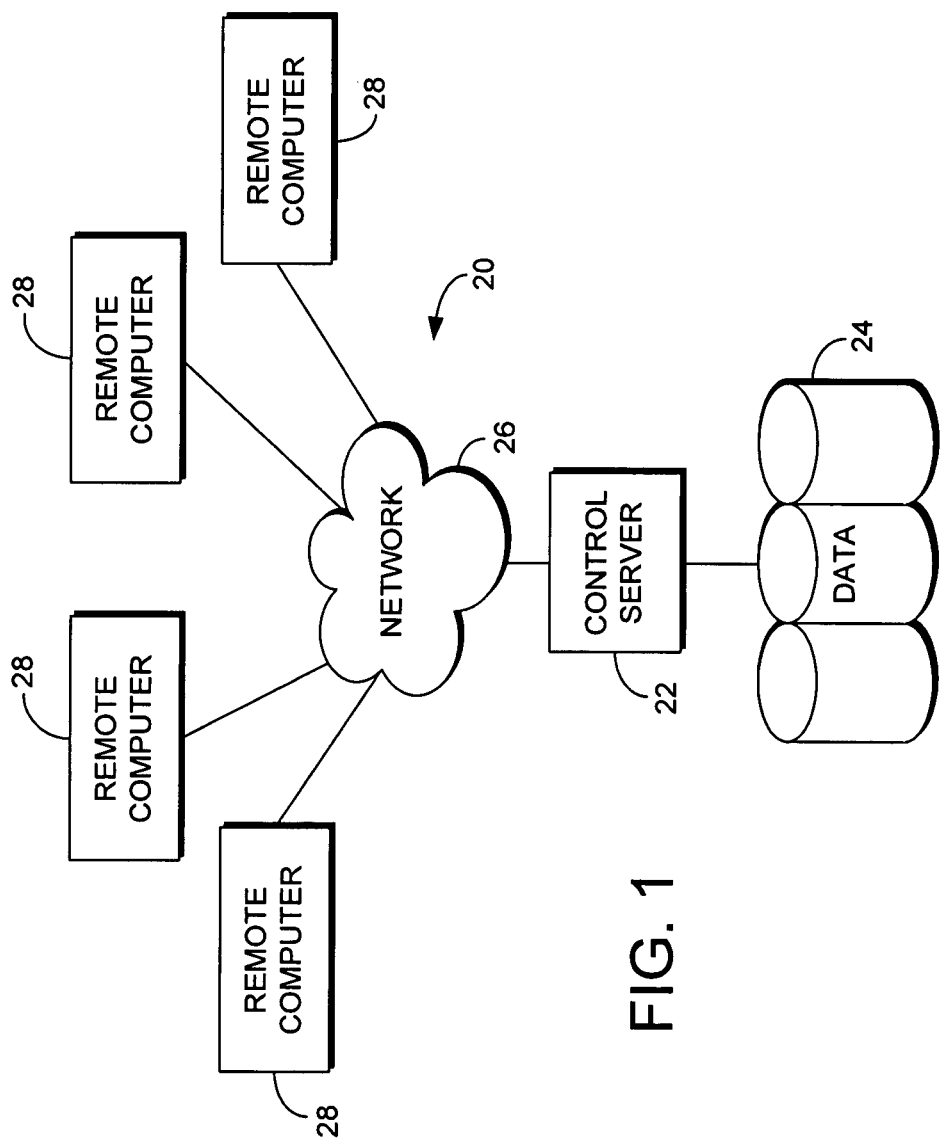
FIG. 1 is a block diagram of an exemplary computing environment suitable for use in implementing the present invention.
Figure 6:
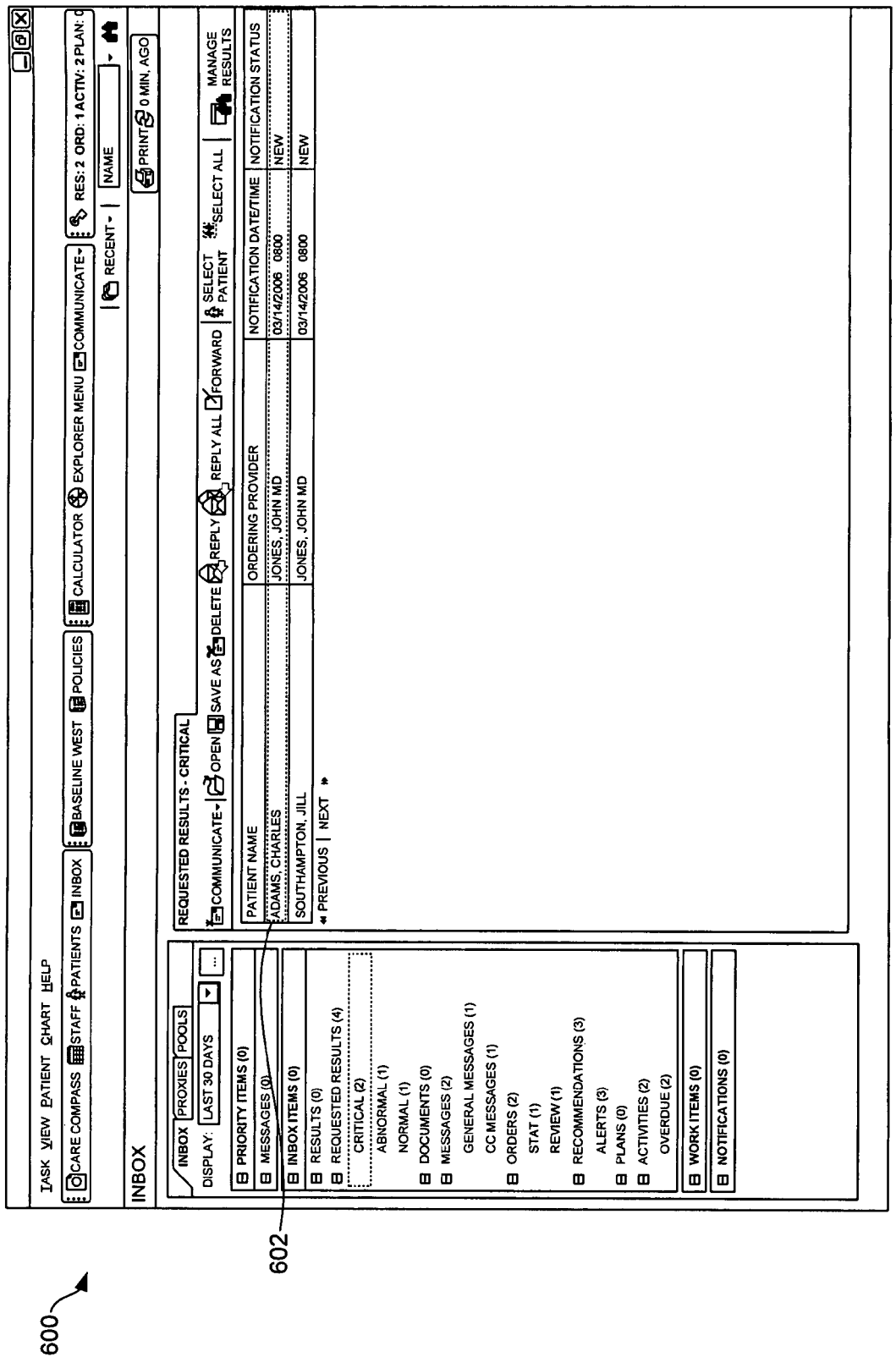
FIG. 6 is an illustrative screen display showing an inbox accessed from a key notification on a patient activity list in accordance with an embodiment of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Embodiments of the present invention, among other things, provide computerized methods, systems, and user interfaces for facilitating clinicians in the management of patient activities. An activity or "task" is an assignment or reminder to the clinician that, for instance, a medication was, or is, to be given, a vital sign was, or is, to be checked, data was, or is, to be collected, a procedure was, or is, to be performed, or the like. Activities generally have a time associated therewith which may be a particular instance in time or may indicate that the task is continuous, e.g., an IV medication administered over a period of several hours, and specify only an initiation time and/or a monitoring time. Alternatively, if desired, a time associated with an activity may indicate that an activity is to be performed only as needed (i.e., PRN). Activities are typically generated from orders and specify, with particularity, what is to be done for a patient. Thus, if an order states that a patient is to receive four 20 mg doses of medication X, one dose every three hours beginning at 12:00 pm, four activities may be generated: a first activity at 12:00 pm, a second activity at 3:00 pm, a third activity at 6:00 pm, and a fourth activity at 9:00 pm, each activity indicating that 20 mg of medication X are to be administered.

A patient activity list provides a common view for a clinician to review all patients assigned to the clinician in conjunction with the activities for the assigned patients during a particular work period. The activities included in the patient activity list are based on the clinician's role. In some cases, multidisciplinary activities (i.e., activities for other clinicians) may also be presented in the context of the clinician's activities. The patient activity list is designed in a manner to limit the amount of information presented in the common view to reduce noise, but is fully navigable to allow the clinician to access further information, perform documentation, and perform other actions. The clinician may review, reschedule, and document activities in the context of other activities.

Embodiments of the present invention further provide an activities navigator that manages activities the clinician has selected to complete. The activity navigator may be used by the clinician to easily find where the clinician is among activities the clinician has selected to complete for a patient. As such, the activity navigator allows the clinician to extend prioritization within the midst of completing the workflow. Interruptions may be managed by the activities navigator by saving partially completed activities and allowing the clinician to later access the activities.

Although embodiments of the present invention will be described herein as managing patient activities for clinicians generally, embodiments of the present invention are best suited to managing patient activities for nurses who are tasked with treating patients in a hospital setting.

Referring to the drawings in general, and initially to FIG. 1 in particular, an exemplary computing system environment, for instance, a medical information computing system, on which embodiments of the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

Embodiments of the present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, mini-computers, mainframe computers, distributed computing environments that include any of the above-mentioned systems or devices, and the like.

Embodiments of the present invention may be described in the general context of computer-executable instructions, such as program modules, being executed by a computer. Generally, program modules include, but are not limited to, routines, programs, objects, components, and data structures that perform particular tasks or implement particular abstract data types. Embodiments of the present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 20 includes a general purpose computing device in the form of a server 22. Components of the server 22 may include, without limitation, a processing unit, internal system memory, and a suitable system bus for coupling various system components, including database cluster 24, with the server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 22 typically includes, or has access to, a variety of computer readable media, for instance, database cluster 24. Computer readable media can be any available media that may be accessed by server 22, and includes volatile and nonvolatile media, as well as removable and non-removable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 22. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 24, provide storage of computer readable instructions, data structures, program modules, and other data for the server 22.

The server 22 may operate in a computer network 26 using logical connections to one or more remote computers 28. Remote computers 28 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 28 may also be physically located in non-traditional medical care environments so that the entire health care community may be capable of integration on the network. The remote computers 28 may be personal computers, servers, routers, network PCs, peer devices, other common network nodes, or the like, and may include some or all of the components described above in relation to the server 22. The devices can be personal digital assistants or other like devices.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the server 22 may include a modem or other means for establishing communications over the WAN, such as the Internet. In a networked environment, program modules or portions thereof may be stored in the server 22, in the database cluster 24, or on any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., server 22 and remote computers 28) may be utilized.

In operation, a user may enter commands and information into the server 22 or convey the commands and information to the server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 22. In addition to a monitor, the server 22 and/or remote computers 28 may include other peripheral output devices, such as speakers and a printer.

Although many other internal components of the server 22 and the remote computers 28 are not shown, those of ordinary skill in the art will appreciate that such components and their interconnection are well known. Accordingly, additional details concerning the internal construction of the server 22 and the remote computers 28 are not further disclosed herein.

Embodiments of the present invention will now be described with reference to FIGS. 2-24, which include exemplary screen displays. It will be understood and appreciated by those of ordinary skill in the art that the screen displays of FIGS. 2-24 are provided by way of example only and are not intended to limit the scope of the present invention in any way.

Figure 2:
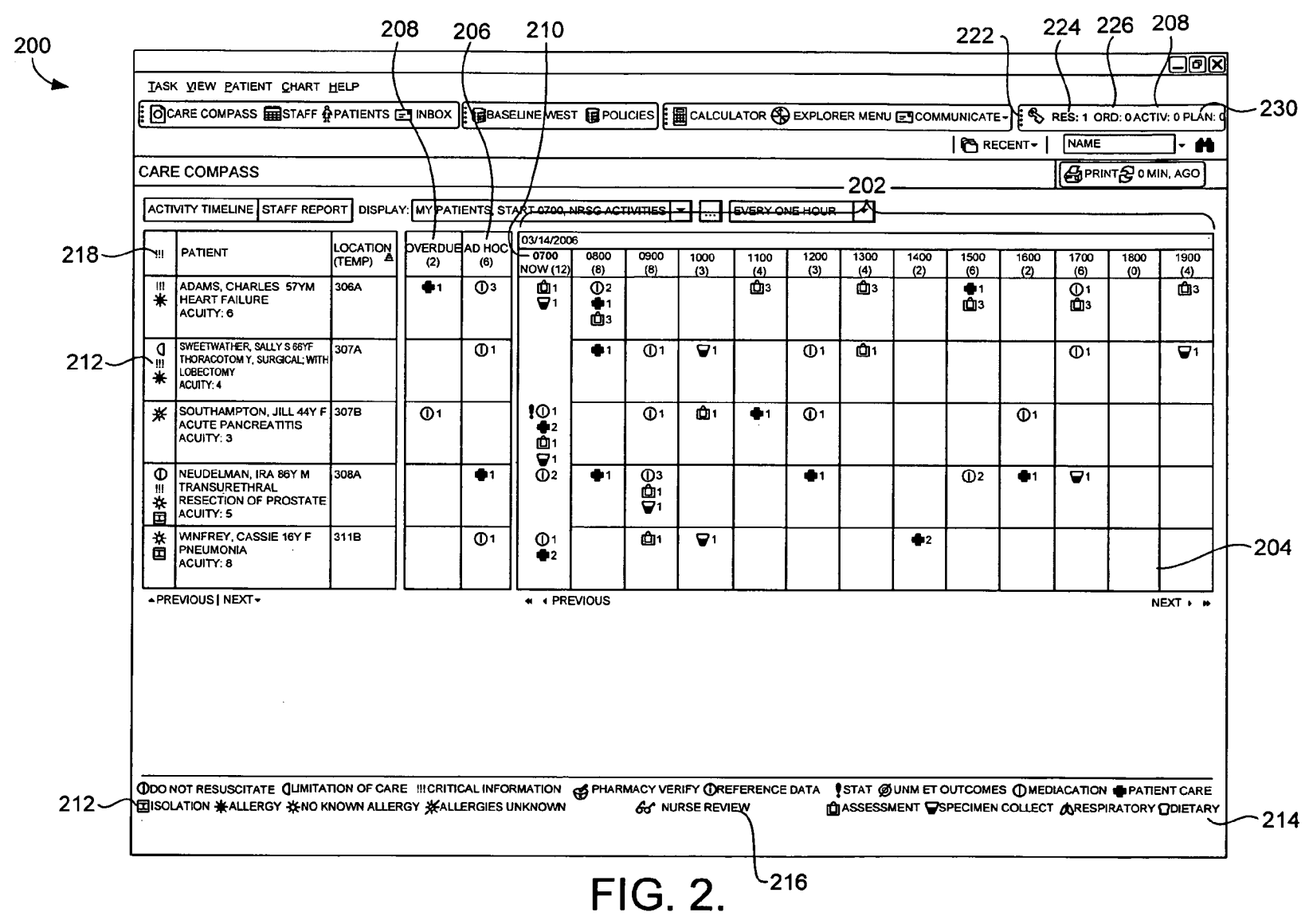

Referring now to FIG. 2, a screen display is provided illustrating an exemplary patient activity list 200 in accordance with an embodiment of the present invention. The patient activity list 200 is populated with the patients that have been assigned to a given clinician and allows the clinician to view the various activities associated with those patients. Activities are presented in the patient activity list with an icon and number to indicate the type of activity and associated number of that type of activity. Accordingly, a full view of activities across the clinician's assigned patients is provided. This allows the clinician to organize and prioritize his/her shift. The activities included in the patient activity list include activities that are relevant to the clinician's role. For example, the patient activity list 200 in FIG. 2 is provided for an ICU nurse, Jan Carter. Accordingly, the activities included are those relevant to an ICU nurse and include, for instance, medications that need to be administered, patient care items, assessments, and specimen collection activities. As another example, activities relevant for a respiratory therapist would include, for instance, ventilator checks. This activity is typically relevant only to therapists who are assigned that activity.

As shown in FIG. 2, the patient activity list 200 provides a timeline view 202 showing when patients have care-needed activities due. Typically, the timeline will include the entire shift for the clinician. For example, a bold, vertical line 204 is provided in the patient activity list 200 to indicate when the clinician's shift ends. In the present embodiment shown in FIG. 2, the timeline is segregated into time periods by hours. However, the timeline may be divided by any time interval within various embodiments of the present invention. An ad hoc column 206 is also provided to indicate any activities that do not have an associated time. For example, as-needed medications, such as pain medications, may be included in the ad hoc column 206. Additionally, an overdue column 208 is provided to indicate any overdue activities.

An indication is provided for each column (overdue activities column 208, ad hoc column 206, and each time period column in the timeline view 202) showing the total number of activities for all patients for that column. For example, an indication of two total activities is provided for overdue activities 208, an indication of six total activities is provided for ad hoc activities 206, and an indication of twelve total activities is provided for the 0700 time period 210. Accordingly, the clinician may readily identify slower and busier periods of the shift and prioritize as necessary. Further, an indication may also be provided to identify the current time period. For instance, the column for the 0700 time period 210 has been highlighted and an indication of "Now" has been provided in the patient activity list 200 to indicate that it is the current time period.

In some embodiments, the patient activity list 200 may also provide an indication of when a patient will be off the clinician's unit. For example, the cells corresponding with the patient, Sally Sweetwater, and the time periods, 1400 through 1600, have been highlighted to indicate that the patient is off the unit during that time period for surgery, consult, procedure, etc. In some embodiments, the clinician may select that time period to access information associated with the patient's location during that time. As such, the clinician can view when activities do not need to be done for the patient, can prepare for the patient to leave the unit (e.g., prepping the patient for surgery), and/or can prepare for the patients return to unit (e.g., patient may need increased pain medication returning from surgery). Additionally, the clinician can balance his/her workload and complete activities for other patients while the patient is off the unit.

The patient activity list 200 is organized in a simplified manner that allows the clinician to readily identify patient activities while not being overloaded with extraneous information. For example, graphical icons are used to represent activities, critical indicators (which will be described in further detail below), and other miscellaneous items. The legend at the bottom of the screen provides definitions for the various icons. In particular, the legend provides definitions for critical indicator icons 212, activity icons 214, and other miscellaneous item icons 216. It will be appreciated that any variety of icons may be utilized. Although the patient activity list 200 limits the amount of information included in the normal view, the patient activity list 200 is fully navigable allowing the clinician to access further information as necessary, as well as to reschedule and document activities.

Patient information is provided in the patient activity list 200 for each of the clinician's patients. To reduce noise, typically only general patient information is provided in the patient information section. For example, in FIG. 2, the patient information includes a patient name, age, sex, medical condition, and an acuity score. Additionally, the patient's location, such as a hospital room number, is provided. In some embodiments, only a patient name or identifier may be included in a patient activity list, while in other embodiments, more detailed information may be included.

In conjunction with the general patient information, critical indicators 218 may be provided with each patient. The critical indicators provide an indication of critical information associated with each patient. By way of example only and not limitation, the critical indicators may include information associated with allergies, code status, isolation, and other vitally important information associated with each patient.

Figure 3:
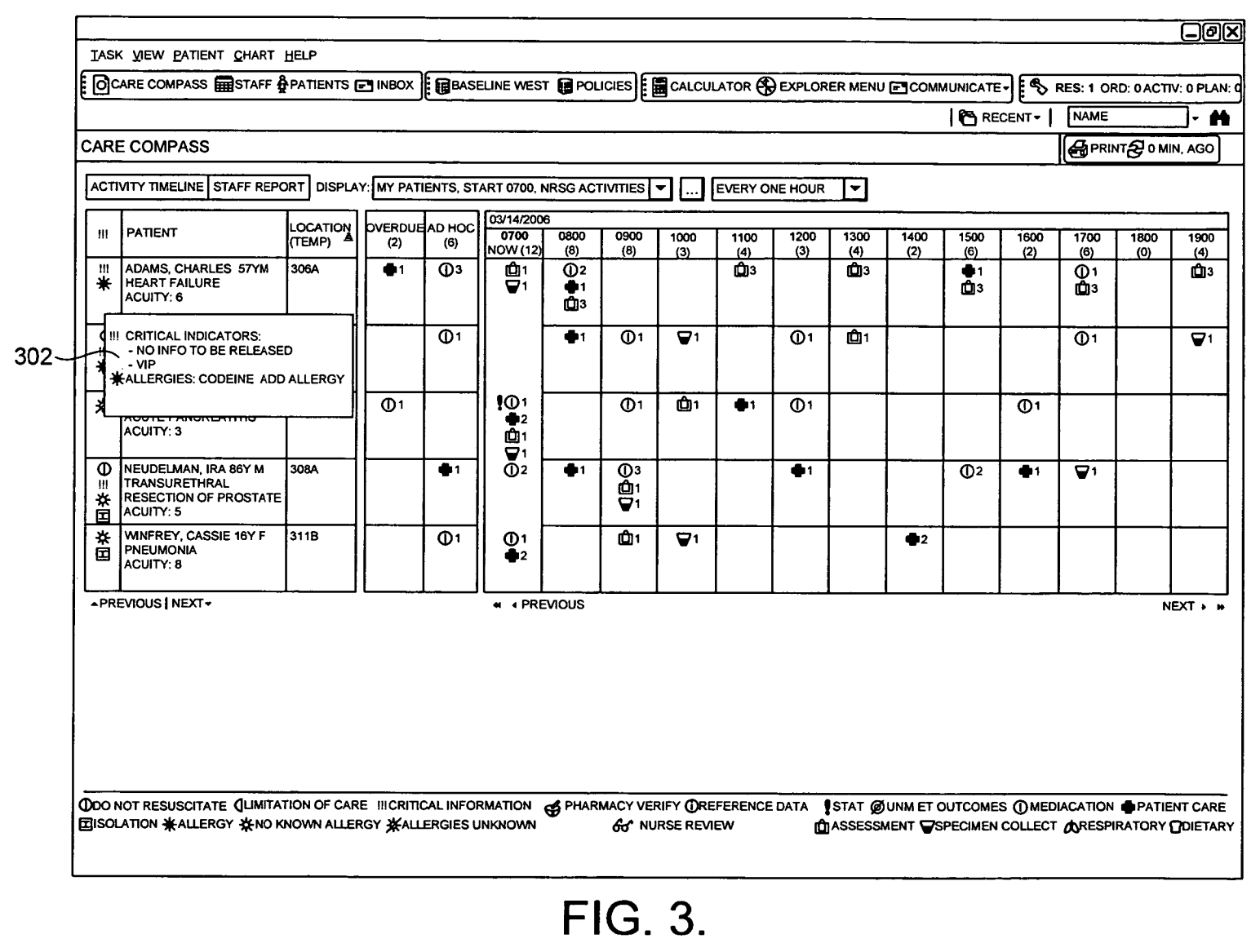

As shown in FIG. 2, zero or more critical indicator icons are provided with each patient. A clinician may quickly identify the type of critical indicator associated with an icon by referring to the critical indicator definitions 212 at the bottom of the display. A clinician may also access specific information associated with a particular patient's critical indicators by selecting that patient's critical indicators. For example, by viewing the patient activity list, the clinician recognizes that there are two critical indicators associated with her patient, Charles Adams, including critical information and allergies, and may wish to review specifics regarding these critical indicators. When the clinician selects the critical indicators 220, the critical indicator window 302 shown in FIG. 3 is presented. As shown in FIG. 3, the critical indicator window 302 includes information associated with both the critical information and allergy critical indicators for the patient. More specifically, the critical indicator window 302 includes critical information indicating that no information is to be released for the patient and that the patient is a VIP. Additionally, the critical indicator window 302 provides information indicating that the patient is allergic to codeine. In some cases, the critical indicator window 302 may allow a clinician to add additional information associated with critical indicators. For example, the critical indicator window 302 provides a link to allow the clinician to add additional allergies if any are determined.

In some cases, a clinician may wish to access further information associated with a patient in addition to the information displayed in the patient activity list. Typically, this would require a clinician to enter the patient's chart to find the desired information. However, the patient's chart often includes a large amount of information, thereby requiring the clinician to search numerous sections of the chart to find the desired information. Embodiments of the present invention provide a patient snapshot that includes relevant information for the patient. The patient snapshot includes information that the clinician may wish to frequently and/or quickly access. Currently, nurses often manually record vital patient information on a note card or other slip of paper, which is often referred to as the nurse's "brain." The "brain" allows the nurse to quickly find vital patient information. Additionally, the "brain" provides a convenient way for a nurse to transfer and exchange important information to an incoming nurse during a shift change. Accordingly, the patient snapshot in accordance with embodiments of the present invention provides an electronic version of such a nurse's "brain" by capturing and providing quick access to vital patient information and comments.

Figure 4:
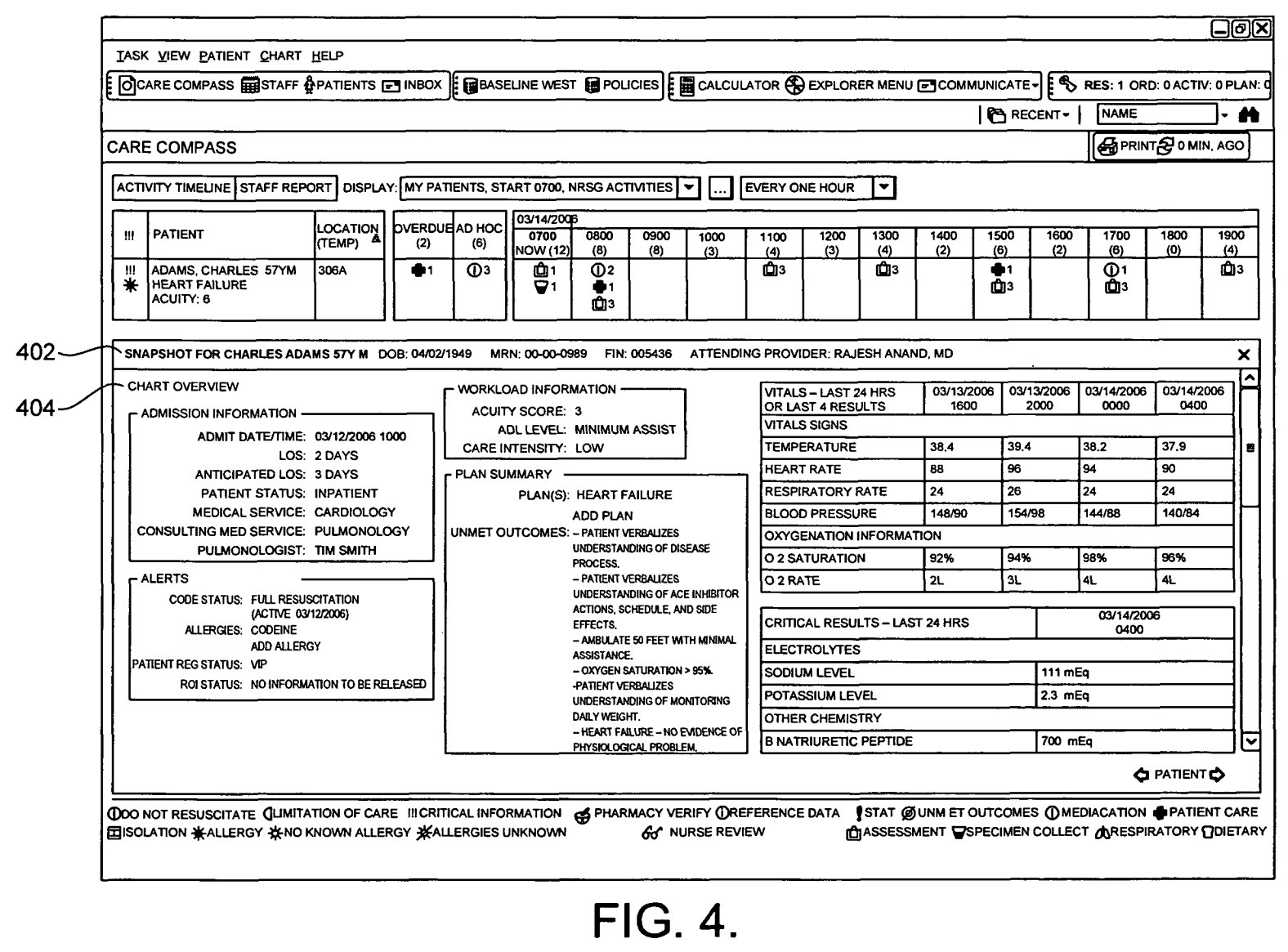

A clinician may view a patient snapshot by selecting a patient from a patient activity list. For example, when the clinician selects the patient, Charles Adams, in the patient activity list 200 of FIG. 2, the patient snapshot 402 shown in FIG. 4 is presented within the display. The patient snapshot 402 may include a variety of pieces of relevant patient information, such as, for example, admission information, alerts, workload information, plan summary, vitals, critical results IV information, invasive devices, monitors, healthcare provider/physicians, medication information, pending orders, and comments associated with the patient.

As shown in FIG. 4, the patient snapshot 402 is presented in conjunction with the timeline of activities for the associated patient. This allows the clinician to view the snapshot information in the context of the daily activities for the patient. Typically, information associated with patients other than the currently selected patient may be removed from the display to provide space for the patient snapshot 402. However, if a limited number of patients are associated with a clinician or sufficient screen space is otherwise available, the patient snapshot may be presented in the display without removing the other patients from the patient activity list.

Although the patient snapshot provides a convenient way for a clinician to quickly access the most frequently needed and/or relevant information for a patient, in some cases, a clinician may need to access further information not included in the patient snapshot. Accordingly, as shown in FIG. 4, the snapshot window 402 includes a link 404 to a chart overview. By selecting the link, the clinician may be navigated to that patient's chart, such as that shown in FIG. 5. The clinician may then navigate the patient's chart to find desired information.

Referring again to FIG. 2, in addition to providing an indication of patient activities for the clinician, the patient activity list 200 also includes a key notification area 222. Key notifications are further described in U.S. patent application Ser. No. 11/427,623, filed on Jun. 29, 2006, which is herein incorporated by reference in its entirety. Generally, key notifications include electronic notifications of new time-sensitive or otherwise important items of information that have been received for a patient. For instance, the key notification area 222 includes key notifications for critical results 224, new orders 226, new activities 228, and plan changes 230. The key notifications included for a particular patient activity list will depend on the role of the clinician. For example, critical results that need to be reviewed by a physician may not be important to a nurse and would not be included in the nurse's key notifications. Conversely, key notifications specific to nursing are those orders that require nurse review, such as a change in a patient's plan of care with modified expected outcomes. This type of notification would be specific to the nurse caring for the patient, but may not be relevant to any other clinician.

Figure 7:
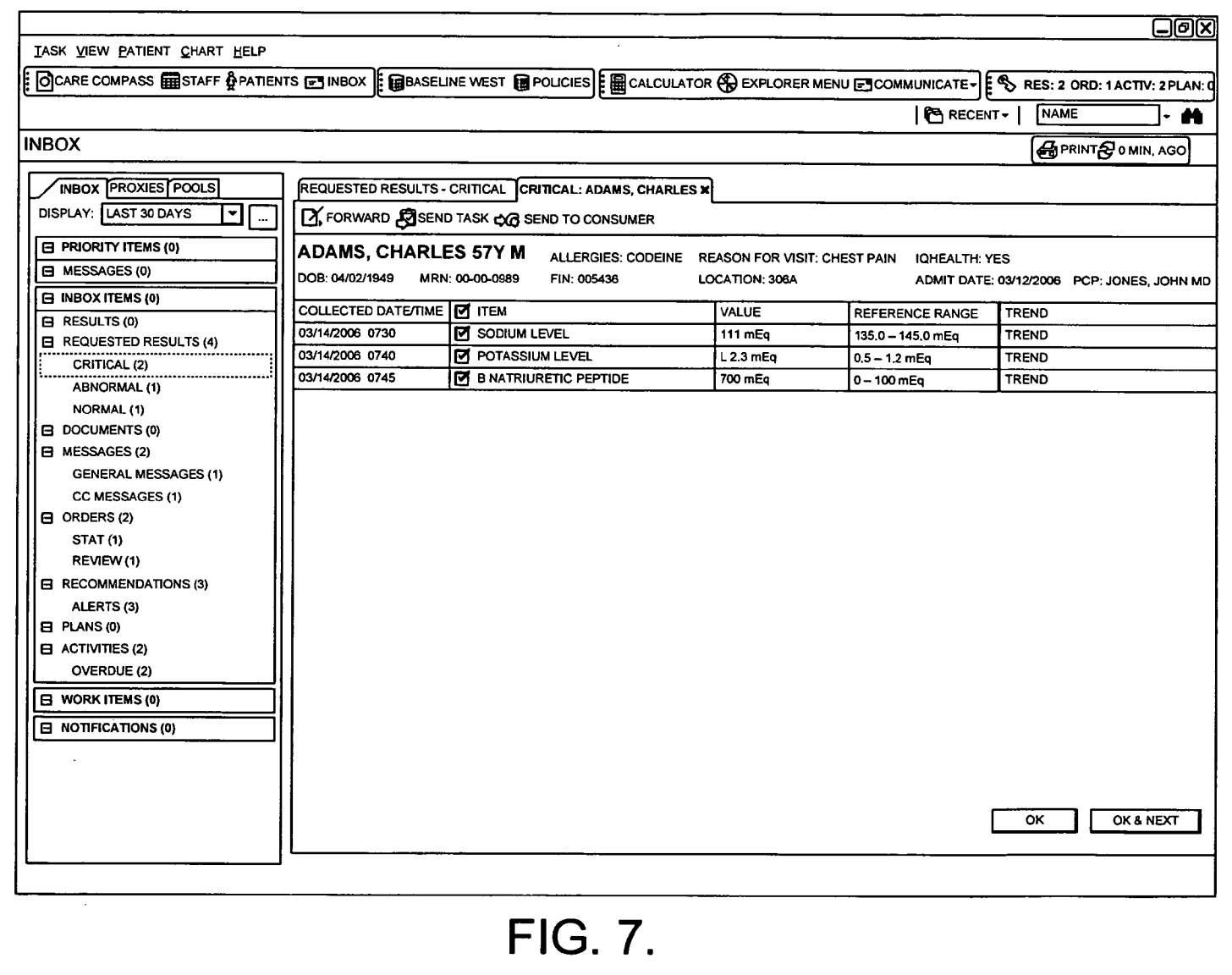

The key notification area 222 allows the clinician to quickly identify new key notifications and to navigate to the associated information. For example, when a clinician selects the critical results notification area 224, an inbox 600 may be presented such as that shown in FIG. 6. In particular, because the clinician selected the critical results notification area 224 in FIG. 2, new critical results are presented within the inbox in FIG. 6. The clinician may select an item, such as the critical result 602 for Charles Adams, to view the relevant information as shown in FIG. 7. For example, the laboratory results, including the sodium level, potassium level, and B Natriuretic peptide, for Charles Adams are complete. These levels are important for a clinician such as a nurse to see promptly when caring for a patient. Once the clinician verifies that the item has been reviewed and/or any necessary actions have been taken, the item is removed from the key notifications area 222 of FIG. 2.

Figure 8:
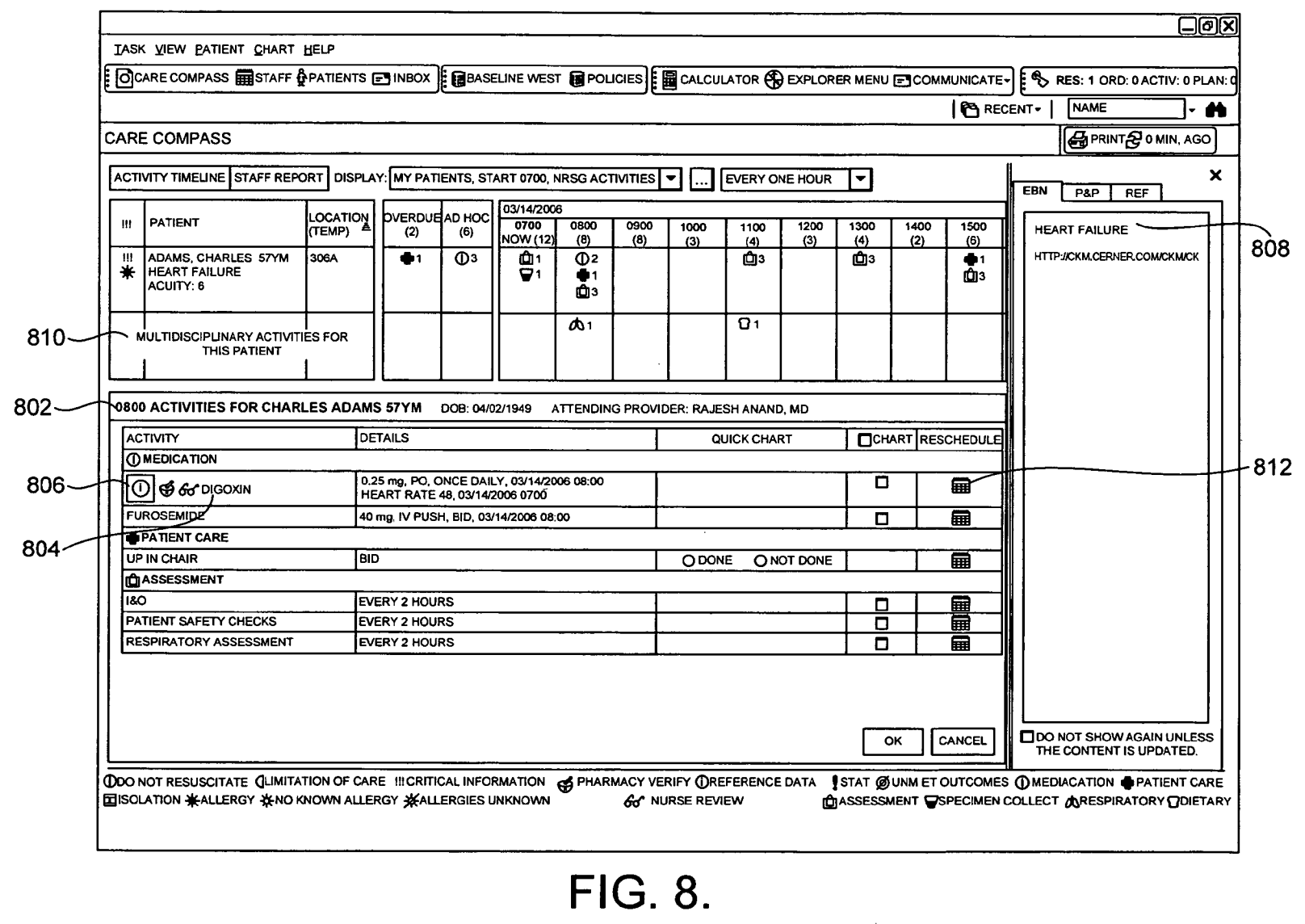

The patient activity list 200 of FIG. 2 allows a clinician to view activities associated with assigned patients. Additionally, the clinician may employ the patient activity list 200 to access information associated with various activities, reschedule activities, and document activities as they are completed. To view information associated with activities, the clinician may select one or more cells within the patient activity list 200. For example, by selecting the cell associated with the patient, Charles Adams, and the 0800 time period, the screen display shown in FIG. 8 is provided. In particular, an action pane 802 is provided showing activities for Charles Adams scheduled for the 0800 time period. In various embodiments, a clinician may select multiple cells and view all activities from those cells within the action pane. For instance, the clinician may have selected the cells associated with the patient, Charles Adams, and both the 0700 and 0800 time periods to view all activities during those time periods.

As shown in FIG. 8, the action pane 802 is provided with the timeline view of activities for the corresponding patient, thereby allowing the clinician to view activity particulars in context of all activities for that patient. Typically, other patients within that patient activity list are removed such as shown in FIG. 8. However, it should be noted that, in some embodiments, other patients may remain within the display.

The action pane 802 provides information associated with the activities within the selected cell of the patient activity list. In FIG. 8, the action pane includes two medication activities, one patient care activity, and three assessment activities. In some case, further information, such as evidence-based data, may be available to the clinician for a particular activity. For instance, the digoxin activity 804 includes a reference data item 806. If the clinician selects the reference data item 806, a reference slider 808 is provided with a link to further information.

Additionally, as shown in FIG. 8, multidisciplinary activities 810 for a given patient may be shown within the patient activity list. The multidisciplinary activities include those activities that are to be performed for the patient by other clinicians, such as, for example, respiratory therapists, physical therapists, and occupational therapists. By viewing activities scheduled to be completed for a patient by other clinicians, the clinician may prioritize when activities are performed to prevent a conflict with other clinicians' activities.

Figure 9:
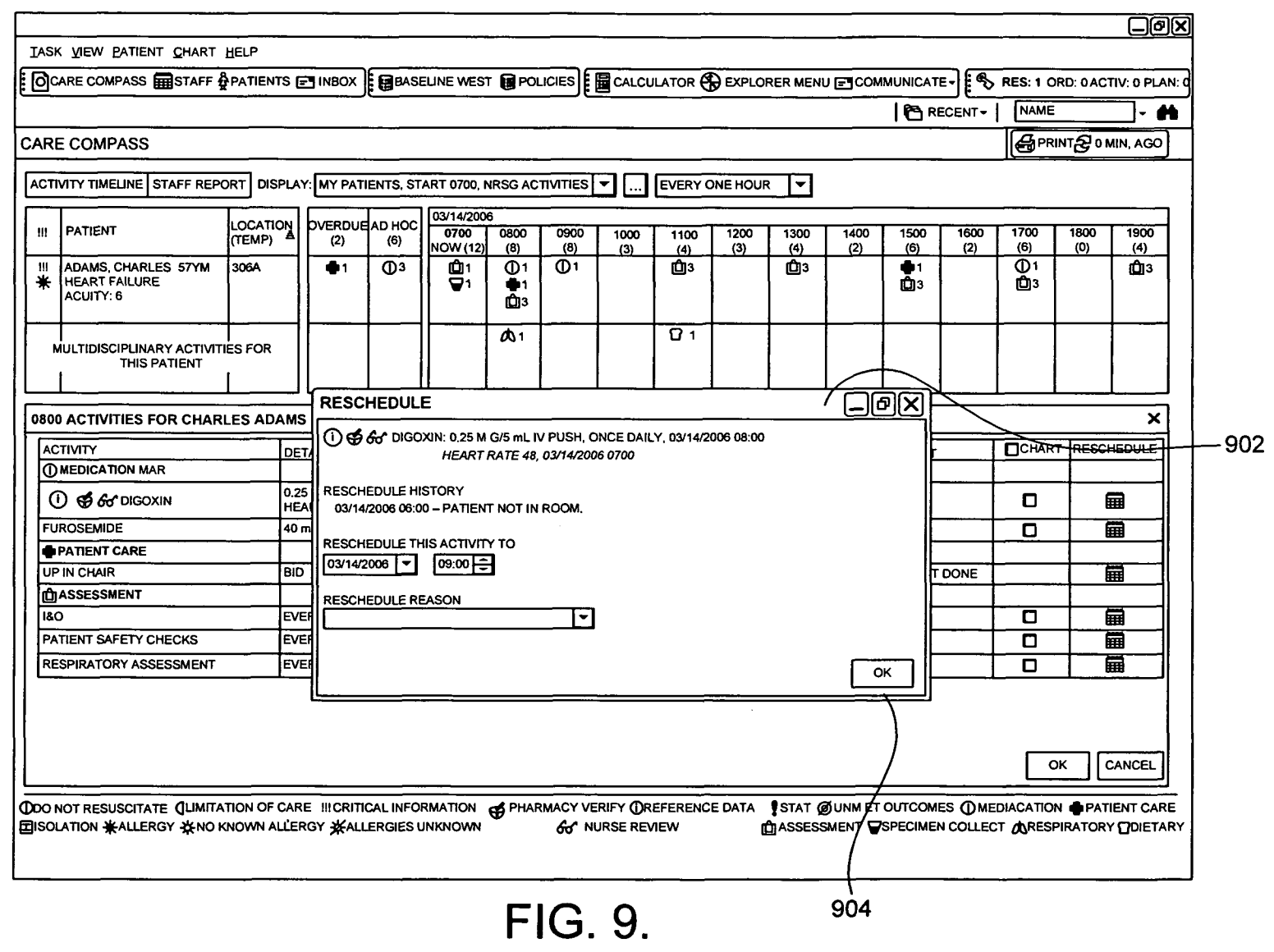

In some cases, a clinician may wish to reschedule a scheduled activity. For instance, when the clinician reviews the patient activity list shown in FIG. 8, the clinician may recognize that it may be difficult to perform all six activities scheduled for the patient during the 0800 time period when there is also a multidisciplinary activity scheduled during that time period. Accordingly, the clinician may reschedule one or more activities using the action pane 802. For instance, the clinician may wish to reschedule the medication activity for digoxin 804. By selecting the reschedule icon 812 associated with that item, a reschedule dialog box 902 such as that shown in FIG. 9 is presented. The reschedule dialog box 902 allows the clinician to reschedule the activity to another time period. For example, the clinician has indicated a reschedule to the 0900 time period. Additionally, the reschedule dialog box 902 prompts the clinician to provide a reason for the reschedule. A reschedule history may also be maintained to track rescheduling of the activities. Accordingly, the reschedule history for the activity is presented in the reschedule dialog box 902. Activity reschedule histories may also be accessed by other personnel for safety, audit, and accounting purposes. For example, a charge nurse may access reschedule histories to detect any inappropriate rescheduling by nurses.

Figure 10:
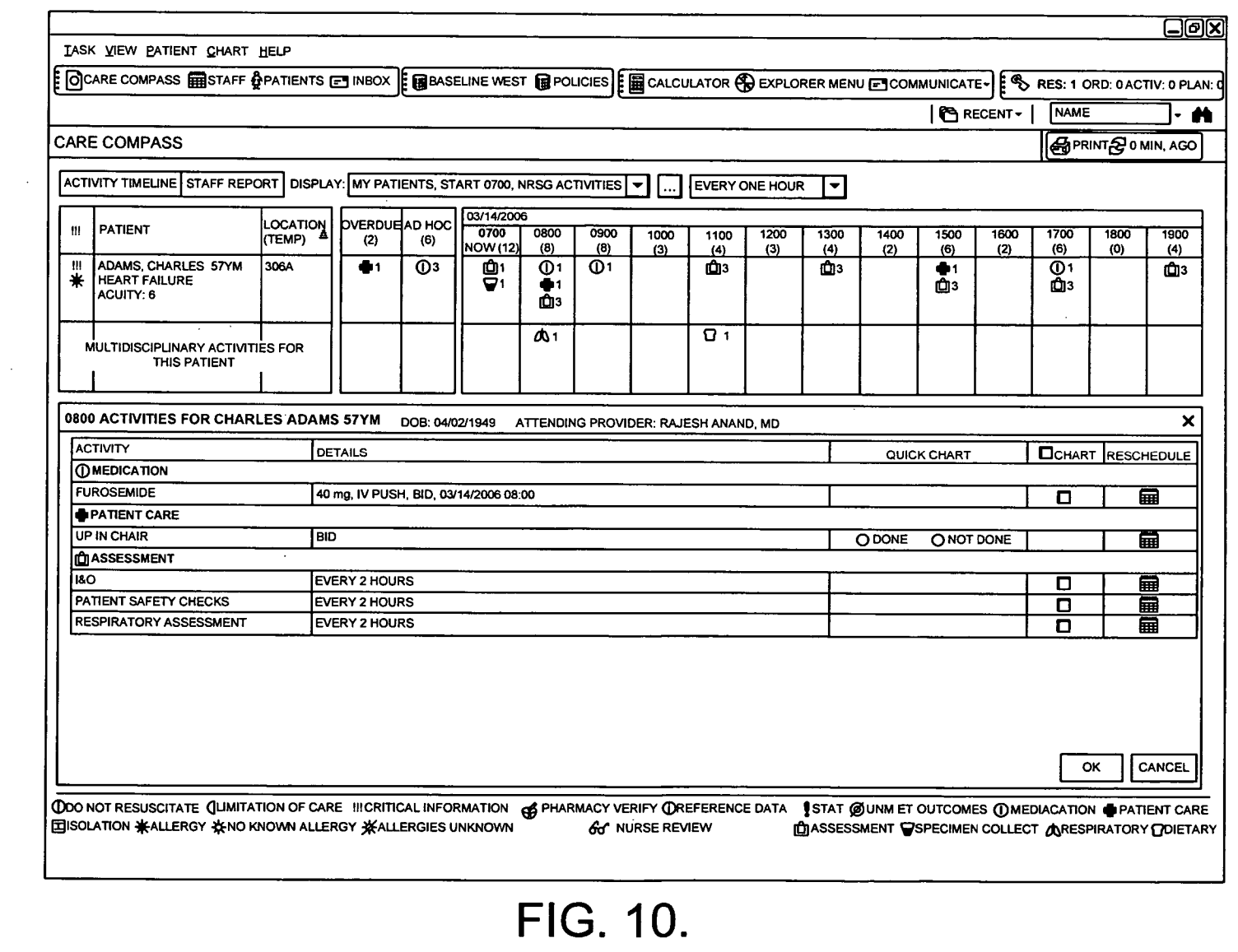

After the clinician indicates a reschedule time period and a reason, the clinician may select the "OK" button 904 in the dialog box. As shown in FIG. 10, the digoxin activity no longer appears in the action pane. Additionally, only one medication activity is now shown for the 0800 time period, and one medication activity is now shown for the 0900 time period. Accordingly, the clinician may reschedule activities while viewing an entire timeline for the patient such that rescheduling may be performed in context of the activities for the patient.

Figure 11:
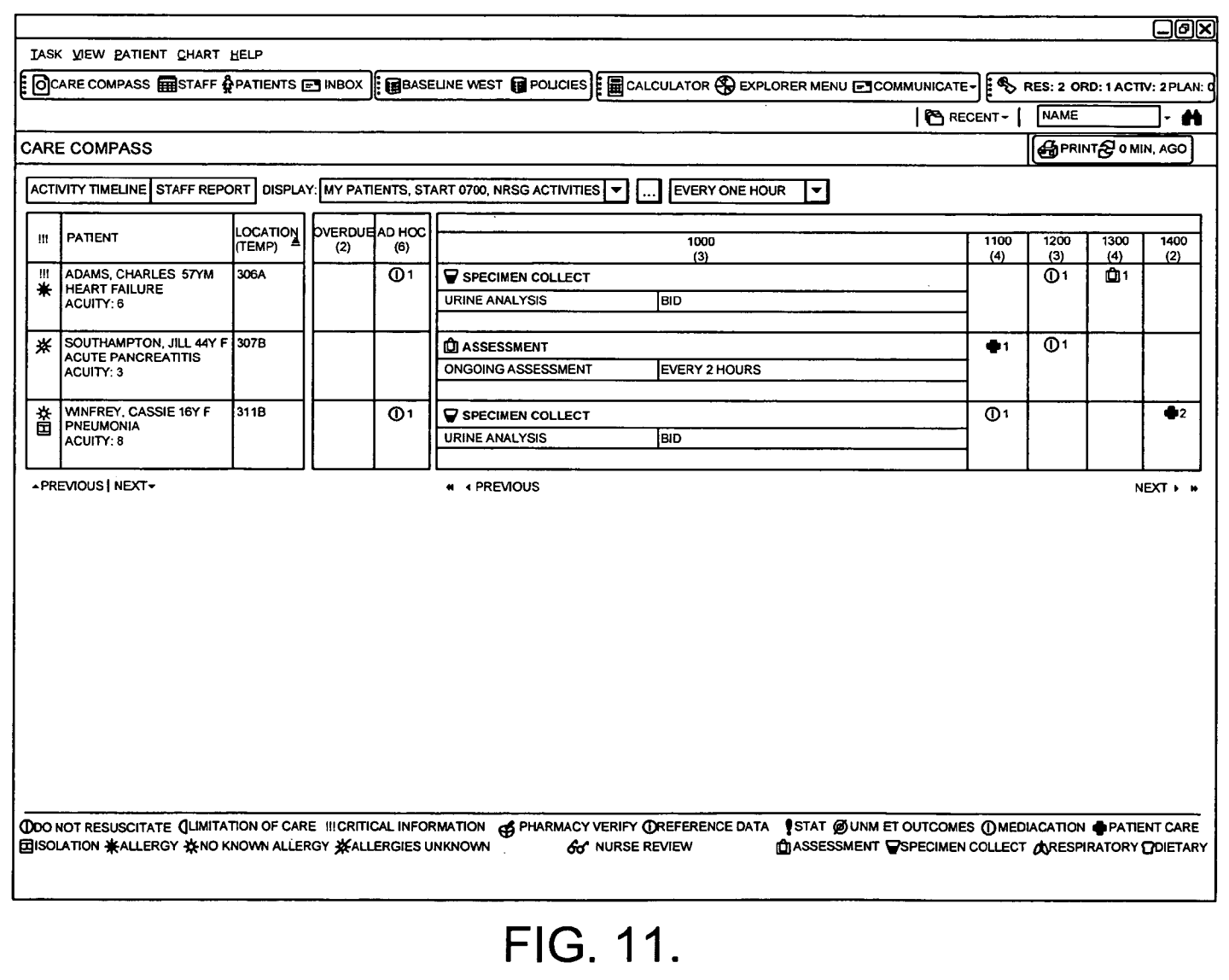

In some cases, a clinician may wish to focus on all activities across assigned patients for a given time period. Accordingly, a column may be selected for review. For example, if the clinician selects the 1000 time period column in the patient activity list 200 of FIG. 2, the filtered patient activity list 1100 of FIG. 11 may be provided. In particular, as shown in FIG. 11, only those patients that have activities during the selected time period are shown in the patient activity list. Other patients are removed to simplify the view. Additionally, further details regarding each of the activities for that time period are provided. As shown in FIG. 11, instead of including only an icon for each activity during the 1000 time period, details of each activity are provided. For example, the specimen collect activity for the patient, Sally Sweetwater is indicated as a urine analysis. The column view allows the clinician to focus on the activities for the scheduled time period to assist in prioritization and organization of the activities.

As indicated previously, a clinician may select multiple cells to view all activities associated with those cells. For instance, referring now to the patient activity list 1200 of FIG. 12, the clinician has selected the cells for Charles Adams corresponding with both the ad hoc activities 1202 and the 0900 activities 1204. Accordingly, all activities associated with these cells are provided in the action pane 1206.

Figure 13:
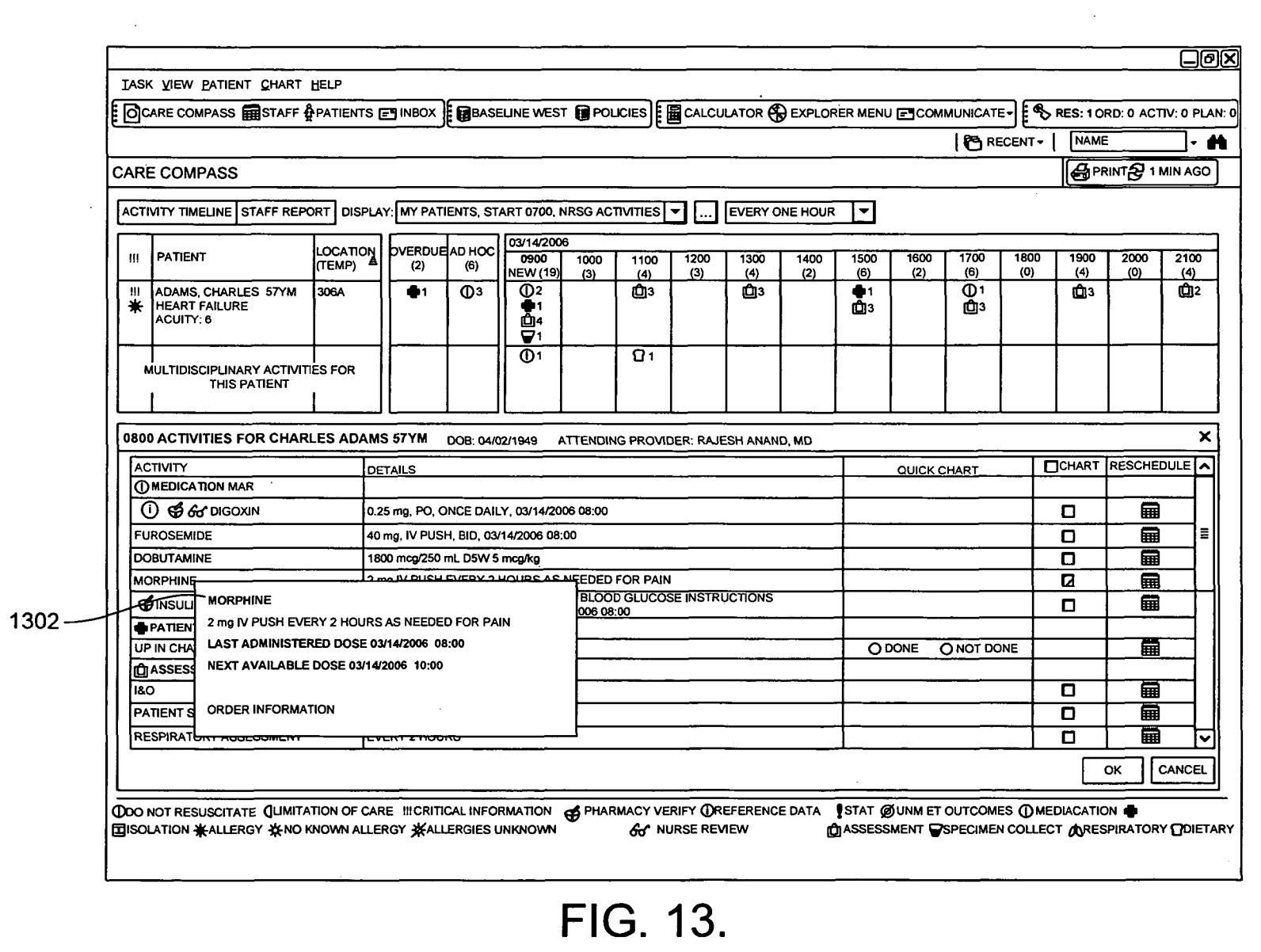
Figure 14:
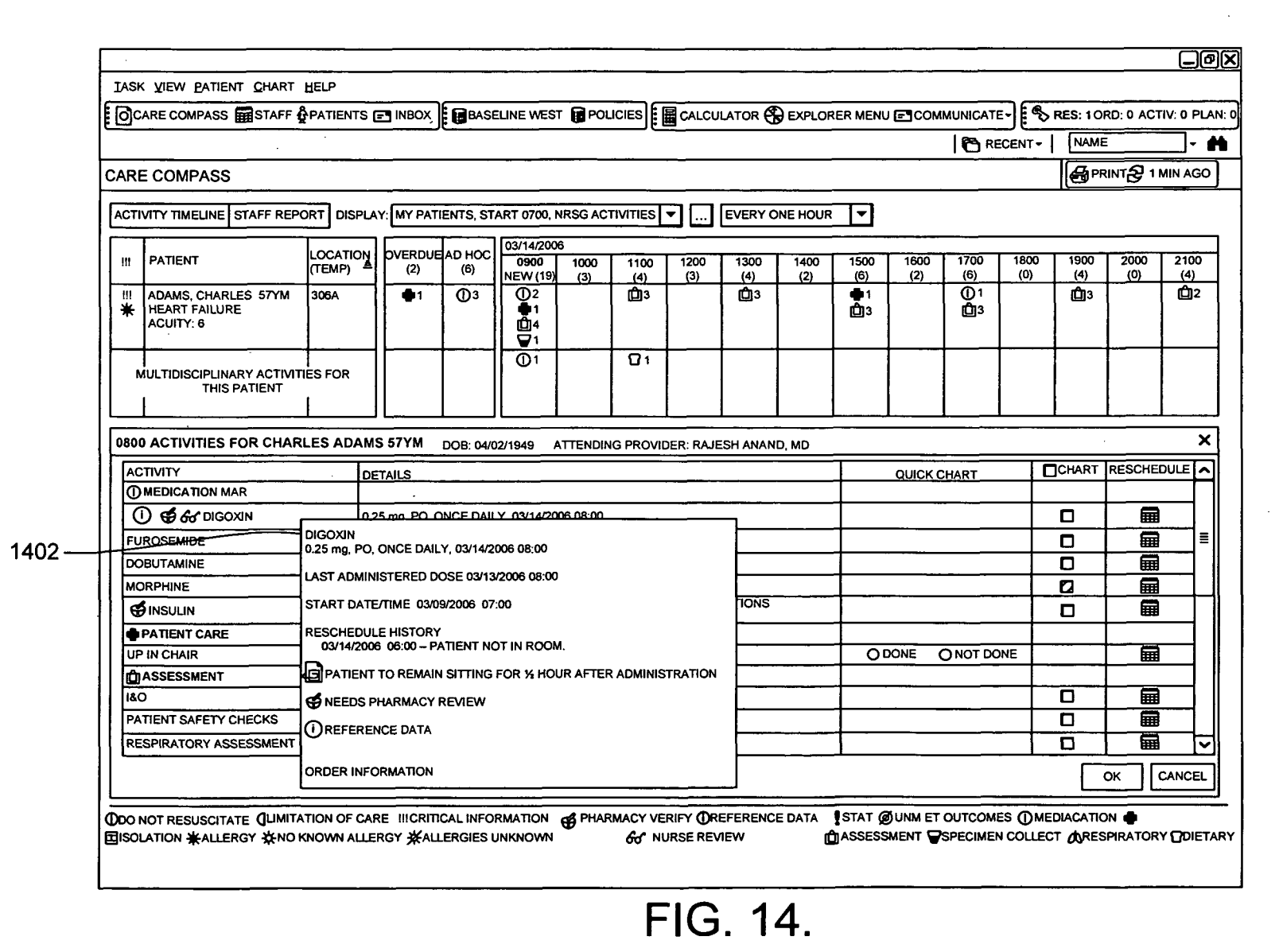

In some cases, further information may be accessed by selecting an activity within an action pane. For instance, when the clinician selects the morphine activity 1208 in FIG. 12, the window 1302 shown in FIG. 13 is provided. In particular, information is provided indicating when the last dose of morphine was administered, as well as the time when the next dose of morphine may be administered. As another example, when the clinician selects the digoxin activity 1210 in FIG. 12, the window 1402 shown in FIG. 14 is provided. In particular, the window 1402 provides information including last administered dose, reschedule history, administration comments, and access to reference information.

Figure 15:
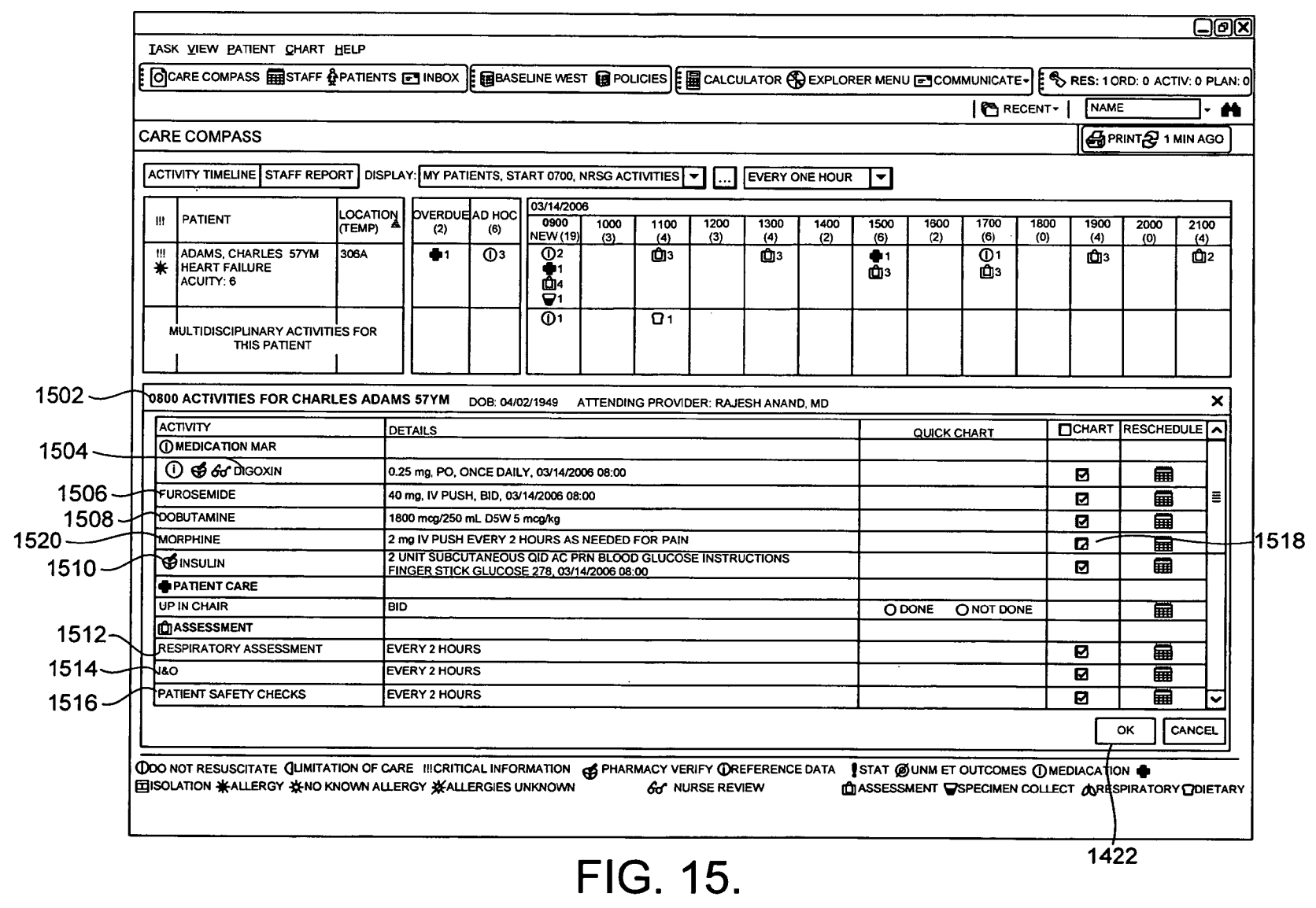

An action pane may also assist the clinician in performing activities and documenting the completion of activities. For example, referring to FIG. 15, the clinician may select the activities in the action pane 1502 that the clinician wishes to perform and document by checking a chart box for each of such activities. As shown in FIG. 15, the clinician has selected to chart the digoxin activity 1504, furosemide activity 1506, dobutamine activity 1508, insulin activity 1510, respiratory assessment activity 1512, I&O activity 1514, and patient safety checks activity 1516. In some cases, safety checks may be provided to prevent a clinician from performing and charting an activity. For instance, the chart box 1518 for the morphine activity 1520 has been disabled. In particular, as shown in the morphine activity details window 1302 of FIG. 13, morphine was recently administered and cannot be administered again until a later time.

Figure 16:
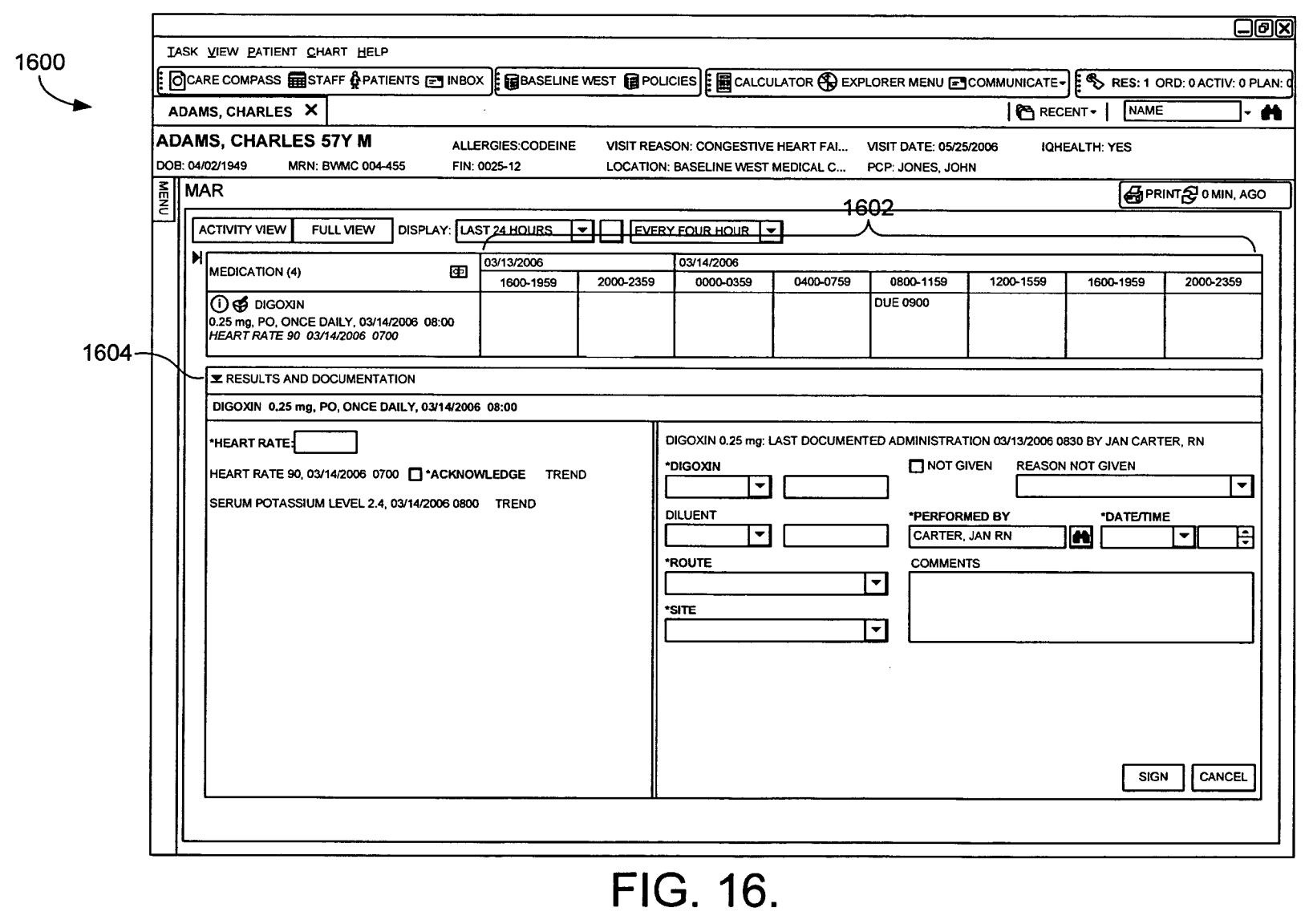
Figure 17:
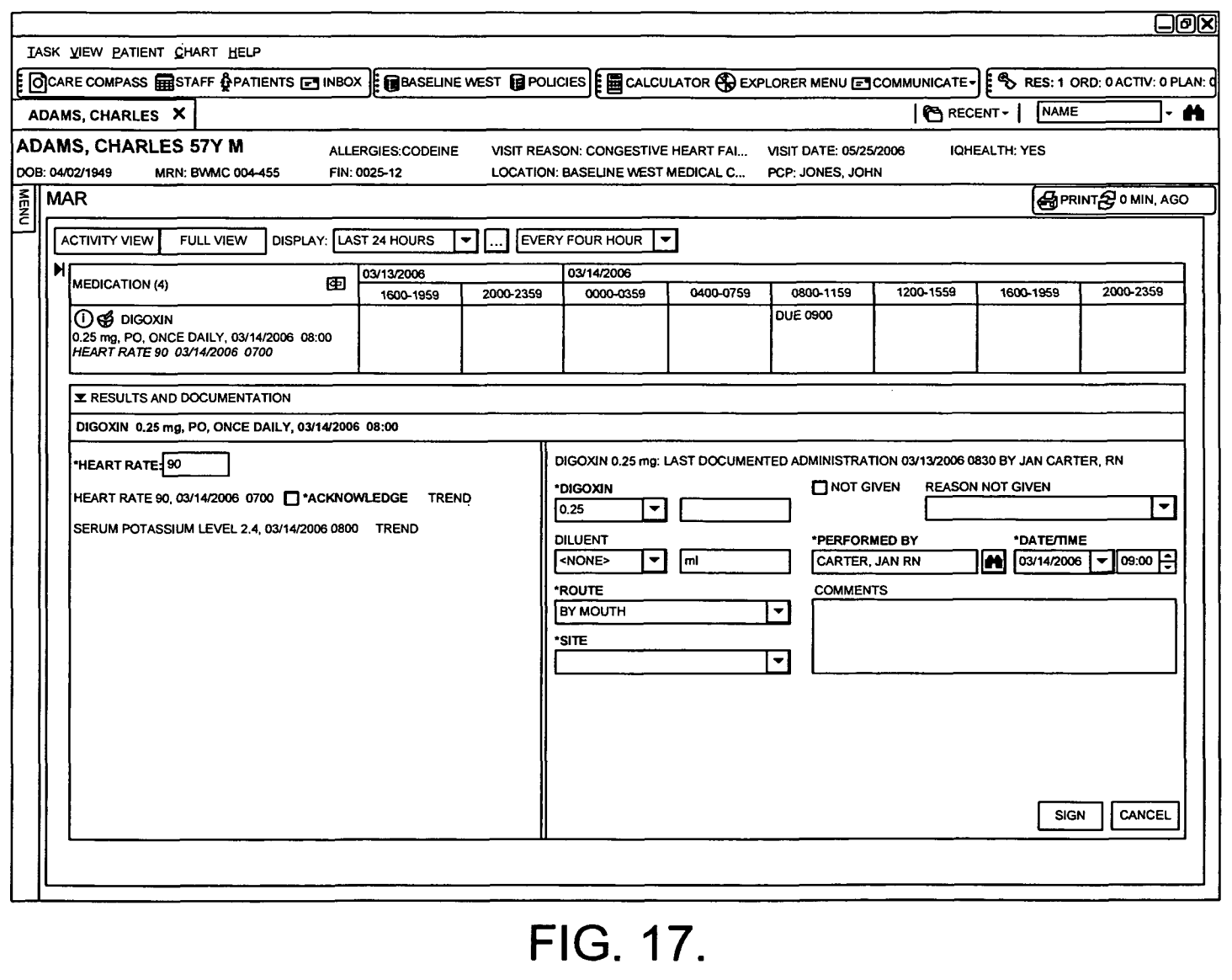

After selecting activities in the action pane 1502 to perform and chart, the "OK" button 1522 may be selected and charting for all the selected activities is initiated. In particular, the clinician is navigated to an appropriate documentation solution. For example, the first activity in the action pane 1502 is the digoxin activity 1504, which is a medication activity. Accordingly, the user is navigated to a medication administration record (MAR) 1600 for the patient as shown in FIG. 16. In particular, an activity view MAR is provided that is specific to the digoxin medication for the patient. The activity view MAR allows the clinician to document within context. For example, a timeline 1602 is included providing an indication of when the medication is due. Additionally, the activity view MAR includes a results and documentation area 1604. Any results relevant to the administration of a medication are included in the results and documentation area 1604. For instance, heart rate and serum potassium level are relevant to the administration of digoxin, and, as such, heart rate and serum potassium level results are presented in the results and documentation area 1604. In some cases, the clinician may need to monitor the patient and provide results to continue documentation. After reviewing the related results, the clinician takes the patient's heart rate and administers the digoxin. Referring to FIG. 17, the clinician documents the patient's heart rate and details of the medication administration.

Figure 18:
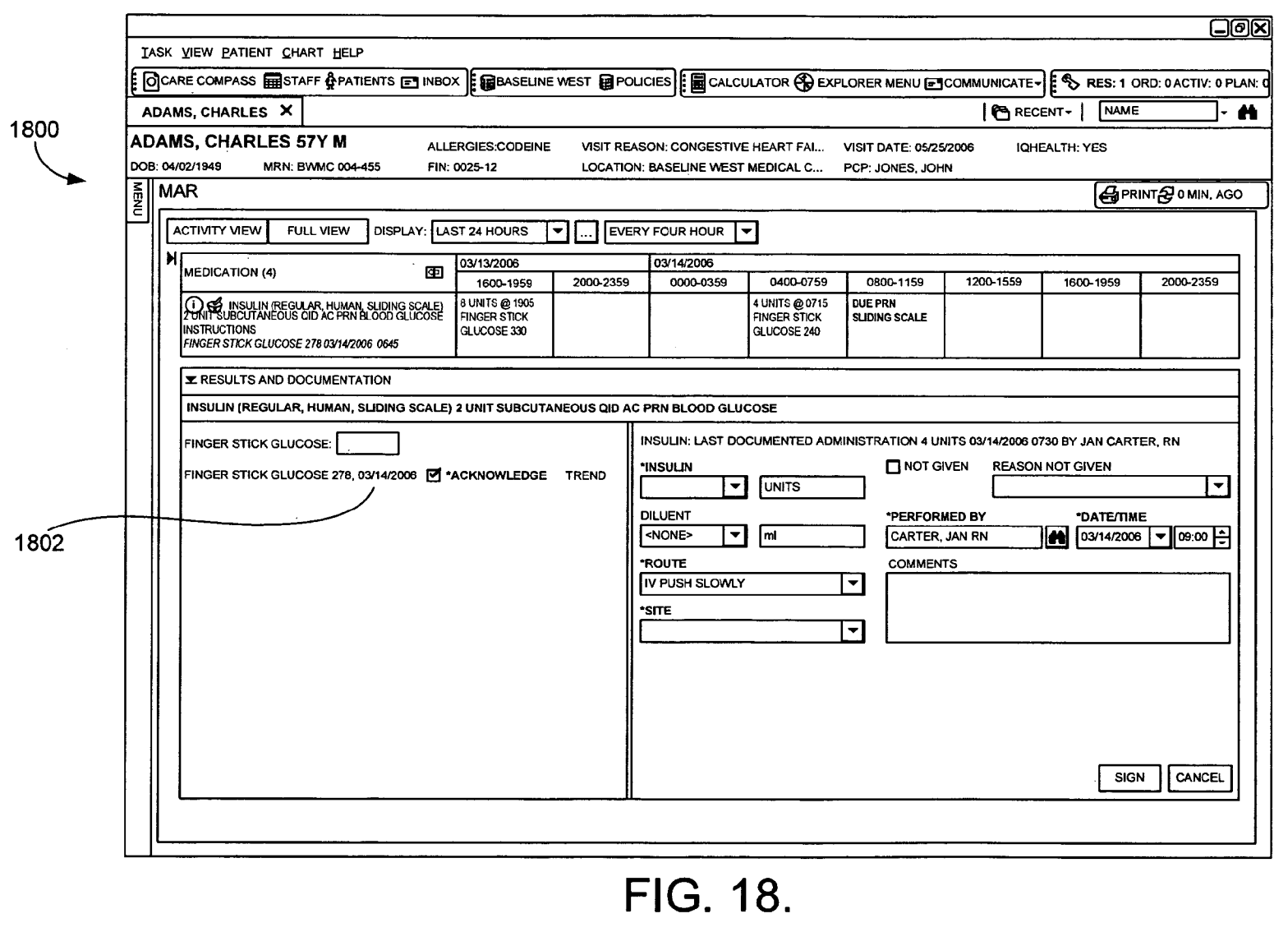

In some embodiments, a clinician may use a related result when documenting an activity. For example, referring now to FIG. 18, an activity view MAR 1800 is presented for insulin. As shown in FIG. 18, related results for the administration of insulin is a finger stick glucose. When the clinician prepares to administer insulin to the patient, the clinician may review the activity view MAR 1800 and recognize that the related result indicates that the finger stick glucose was recently taken for the patient. Accordingly, instead of taking a new finger stick glucose and inserting its results, the clinician may acknowledge the related result in the activity view MAR by selecting the acknowledge box 1802. Accordingly, this related result is used for documentation purposes for the insulin administration.

Figure 19:
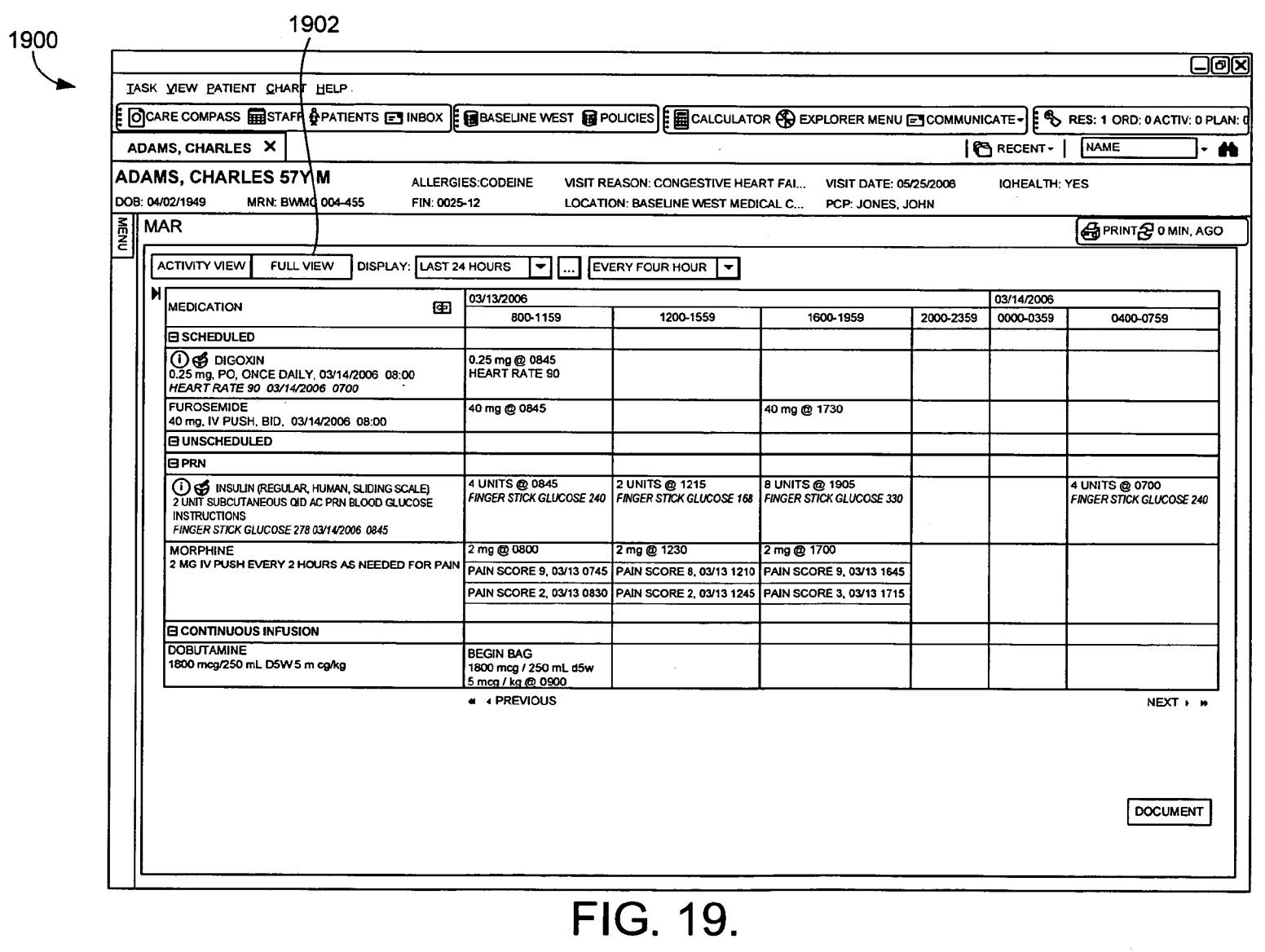

The clinician may further toggle between an activity view MAR and a full view MAR. For example, turning to FIG. 19, a full view MAR 1900 for the patient, Charles Adams, is shown. The full view MAR 1900 may be provided, for instance, by the clinician selecting the "Full View" button 1902. As shown in FIG. 19, the full view MAR allows the clinician to view all medication activities for the patient within context of one another for a specified time period.

At any time, a clinician may view activities that the clinician has selected to document by accessing an activity navigator. This is particularly useful as clinicians are often interrupted while performing and documenting activities. The activity navigator allows a clinician to quickly and easily resume any interrupted activities. For example, if the clinician were interrupted while attempting to complete an assessment of a patient, the clinician may easily return to the assessment with all information previously entered in the assessment documentation having been saved.

Figure 20:
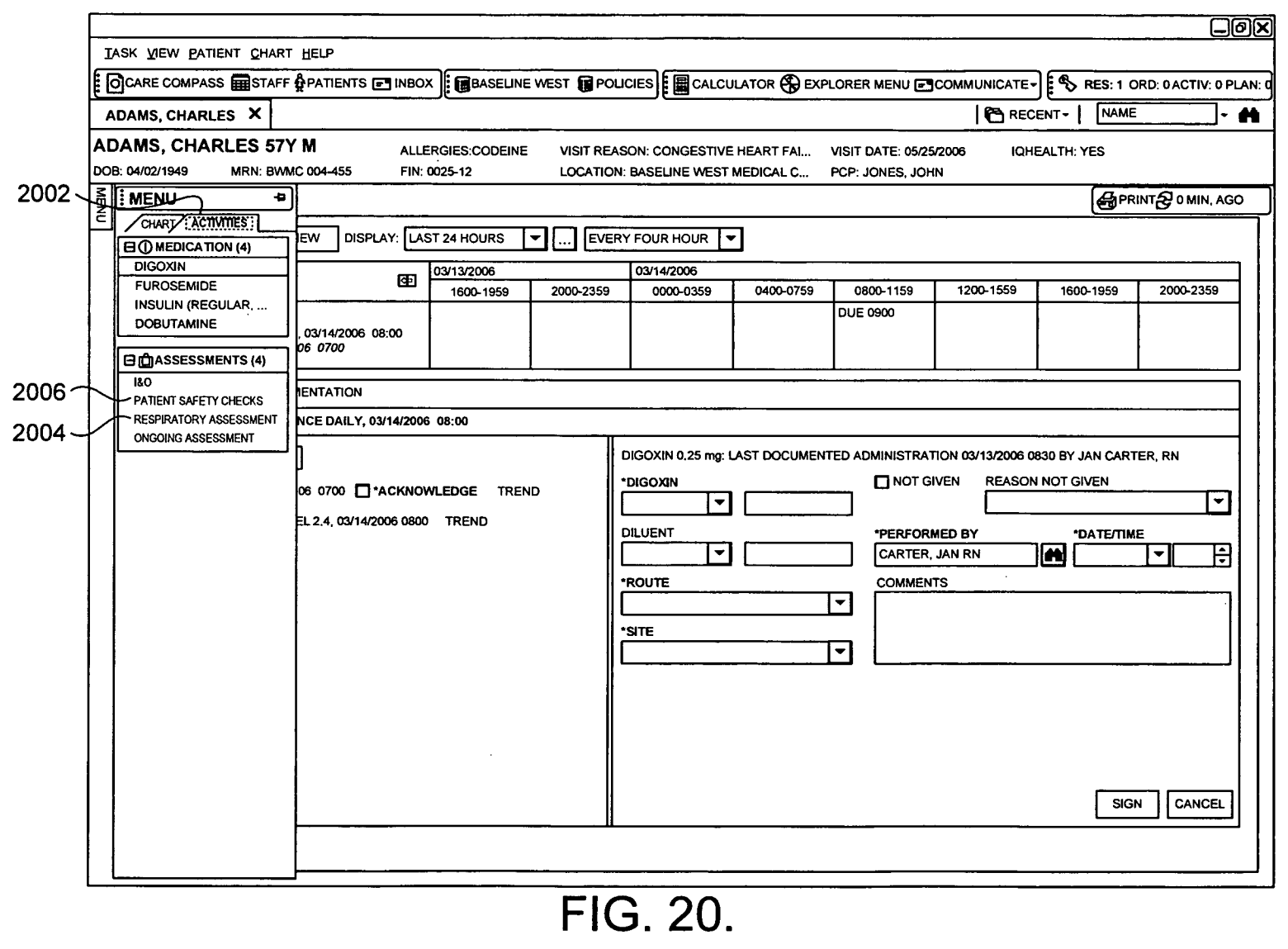

Referring to FIG. 20, a screen display is provided showing an exemplary activity navigator 2002 in accordance with an embodiment of the present invention. As shown in FIG. 20, the activity navigator 2002 indicates each of the activities that the clinician has selected to chart but has not yet completed. By selecting an activity from the activity navigator 2002, the clinician is navigated to the appropriate documentation solution to allow the clinician to continue documenting that activity.

Figure 21:
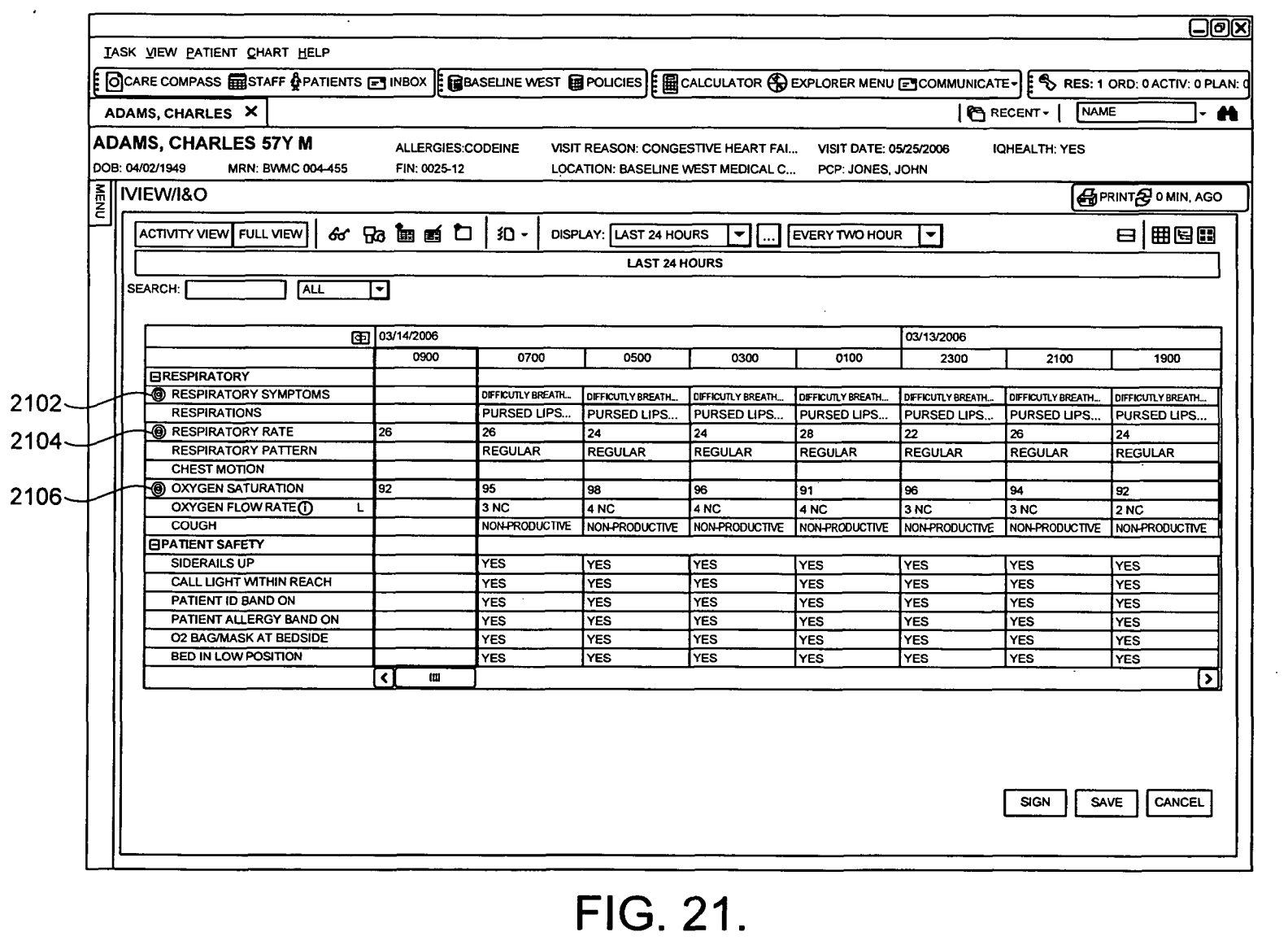

For example, the clinician may decide to select respiratory assessment and patient safety checks 2004, 2006 from the activity navigator in FIG. 20. Based on the selection, the appropriate documentation solution for these assessments is presented to the clinician as shown in FIG. 21. As shown in FIG. 21, the clinician may enter information for the current assessment in context of previous assessments.

Figure 22:
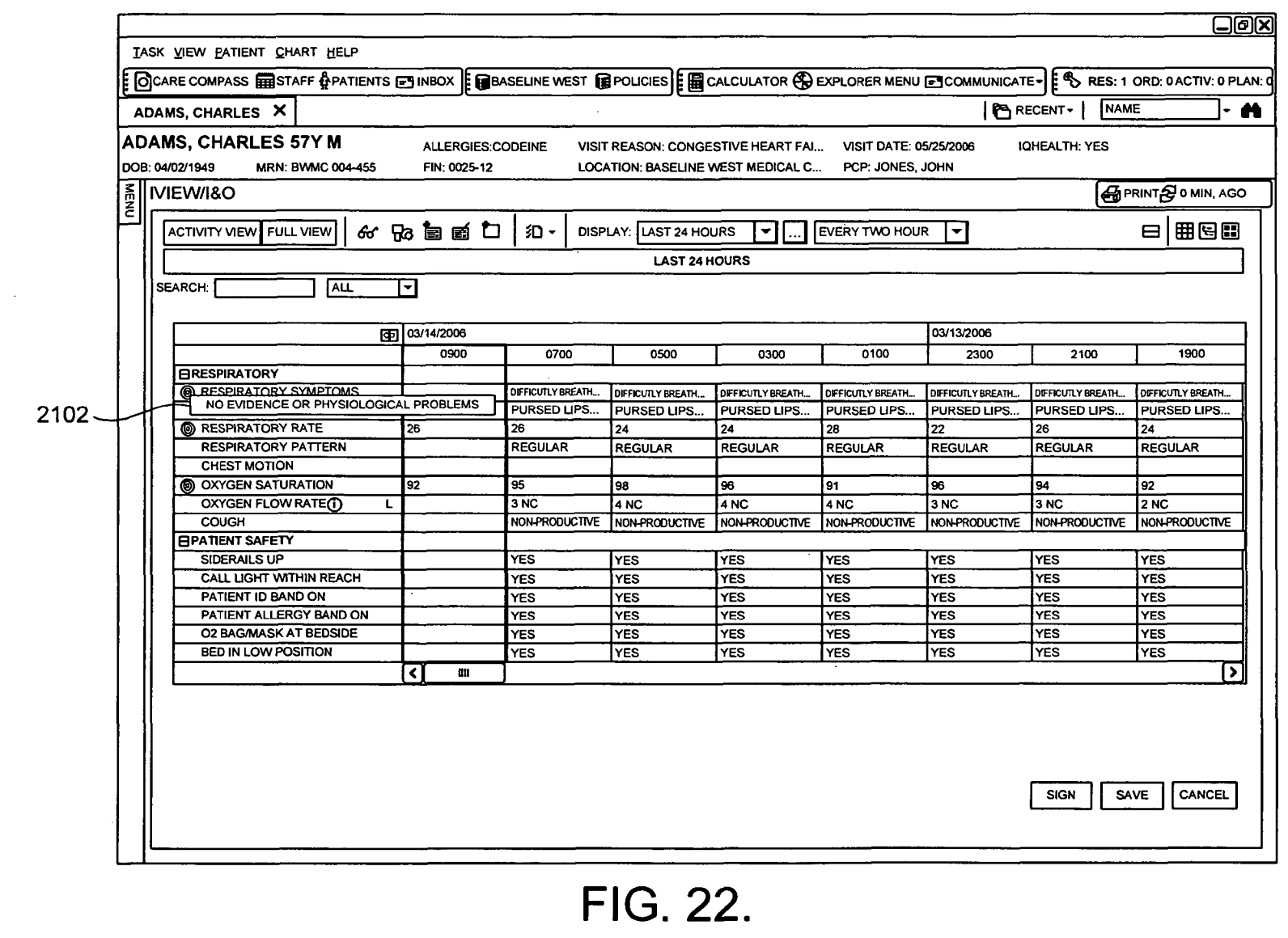

Additionally shown in FIG. 21 are a number of outcome icons 2102, 2104, 2106 that are provided for particular assessment items. The outcome icons 2102, 2104, 2106 provide access to information associated with a patient's plan of care. Typically, a plan of care may be developed for a patient that sets forth a number of outcomes or goals for the patient throughout the care process. Embodiments of the present invention push these outcomes to the documentation workflow. Accordingly, the clinician may review outcomes from the patient's plan of care while documenting assessment. For example, when the clinician selects the outcome icon 2102, the outcome window 2202 shown in FIG. 22 is provided.

Figure 23:
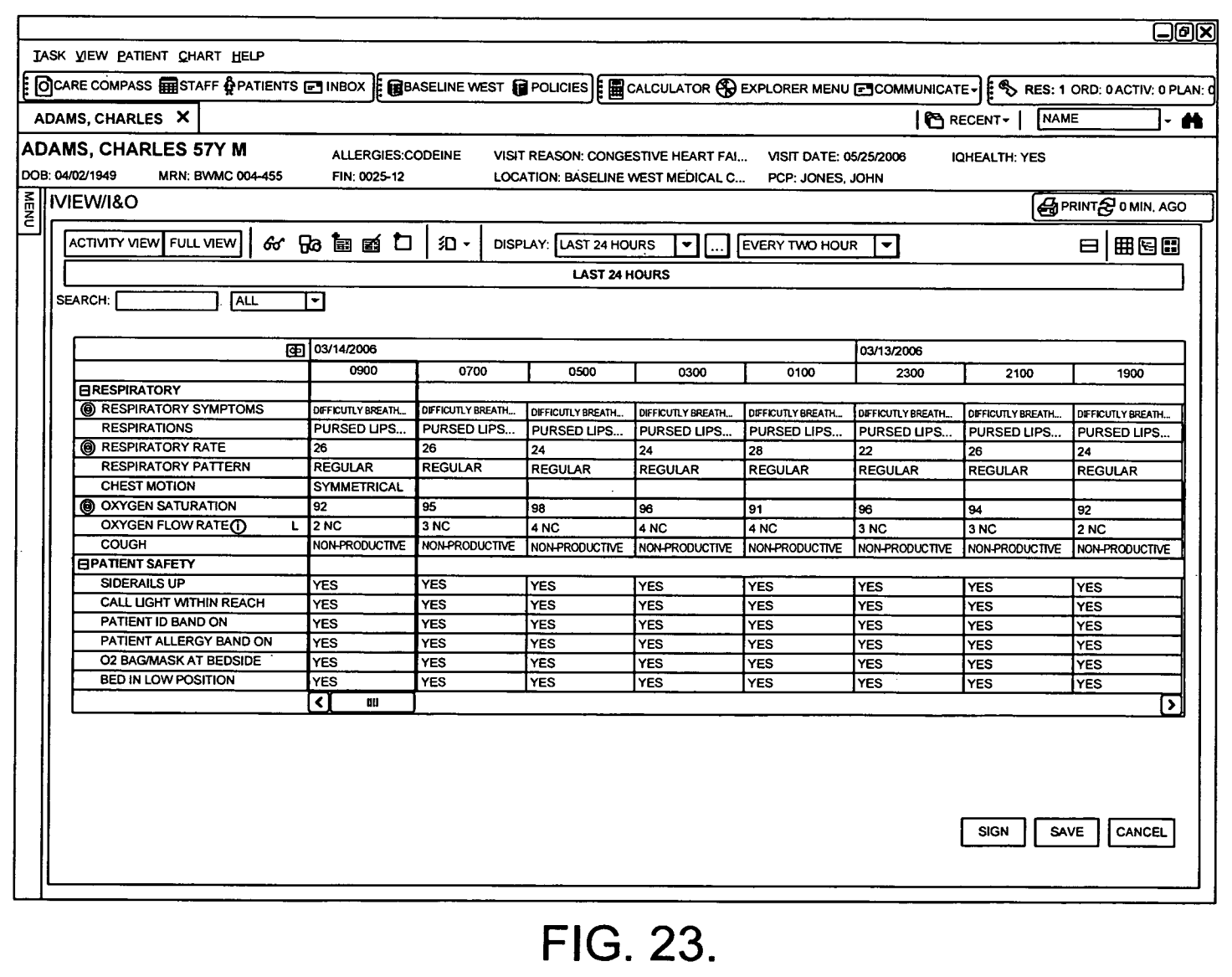
Figure 24:
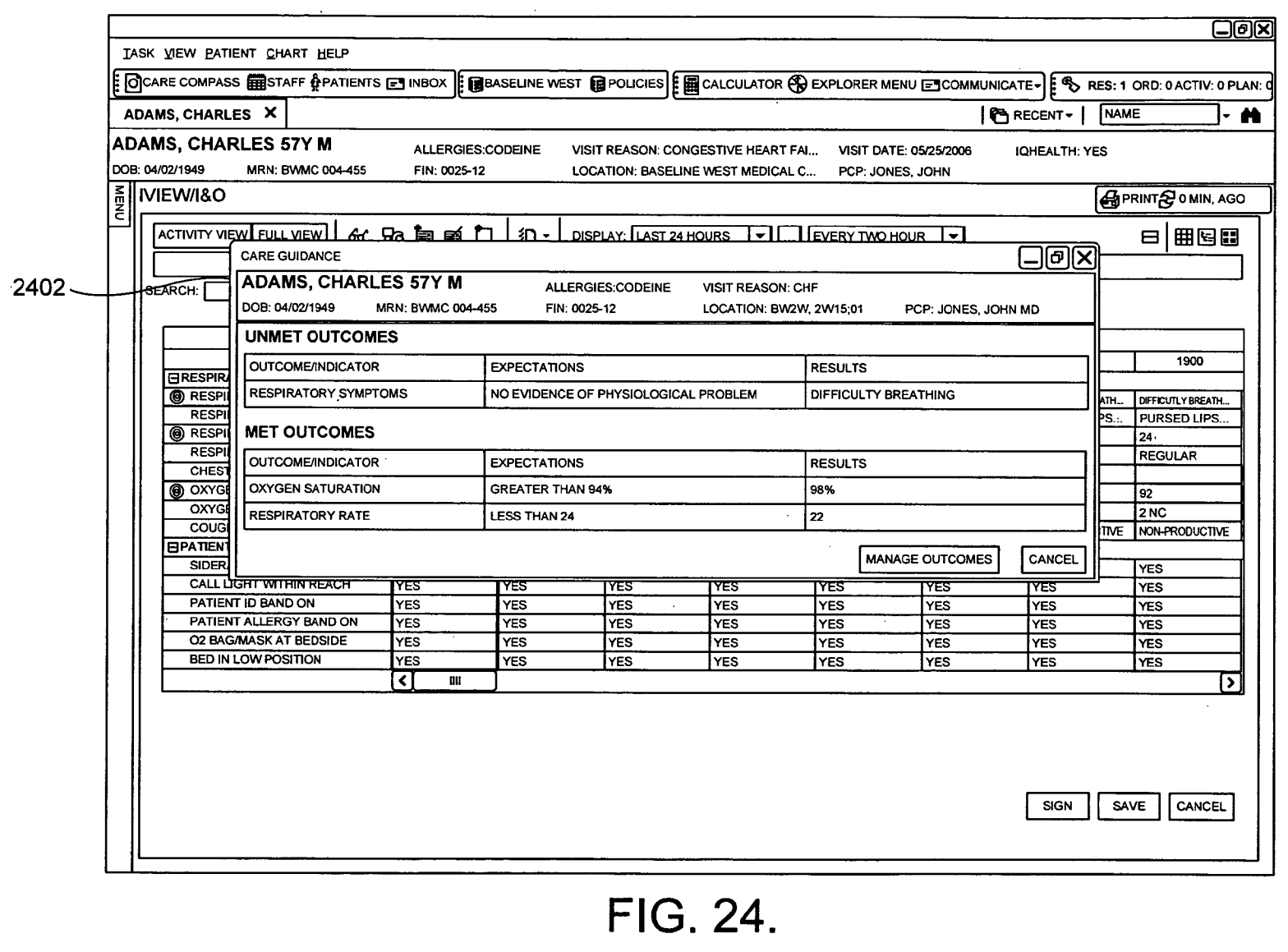

After reviewing outcomes within the documentation, the clinician may complete the assessment documentation as shown in FIG. 23. After completing the documentation, the system may compare the provided assessment information against outcomes from the plan of care to identify met and unmet outcomes. Based on the comparison, the system may provide the summary window 2402 shown in FIG. 24. As shown in FIG. 24, the summary window 2402 provides an indication of met and unmet outcomes. In some embodiments, the summary may be pushed to other clinicians based on role. Additionally, in some embodiments, unmet outcomes may be identified within the patient activity list, thereby allowing the clinician to view the unmet outcomes in the context of other activities for the patient.

As can be understood, embodiments of the present invention provide an approach to facilitate the management of activities for a clinician. The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

What is claimed is:

1. One or more computer storage media, not being a signal per se, storing computer-useable instructions that, when used by one or more computing devices, cause the one or more computing devices to perform a method in a clinical computing environment for facilitating management of activities for a clinician, the method comprising:

presenting a timeline view area having role relevant scheduled activities for plurality of patients assigned to the clinician, wherein the role relevant scheduled activities comprises:

(1) a subset of role relevant scheduled activities for a first patient wherein the subset of role relevant scheduled activities for the first patient comprises a plurality of activities to be performed by the clinician for the first patient from the plurality of patients and (2) a subset of other role relevant scheduled activities for one or more other patients assigned to the clinician, wherein the subset of other role relevant scheduled clinical activities for one or more other patients assigned to the clinician comprises a plurality of activities to be performed by the clinician for the one or more other patients assigned to the clinician, wherein the subset of role relevant scheduled activities for the first patient is presented in a single timeline view based on a scheduled time and in association with other role relevant scheduled activities for the first patient and wherein the subset of other role relevant scheduled clinical activities for the one or more other patients assigned to the clinician is presented in the single timeline view based on a scheduled time and in association with other role relevant scheduled activities for the one or more other patients assigned to the clinician;

receiving a user selection of the first patient;

in response to receiving the user selection of the first patient, presenting one or more multidisciplinary activities for the first patient within the timeline view area, the one or more multidisciplinary activities comprising activities scheduled to be performed by one or more other clinicians for the first patient, each multidisciplinary activity being presented in the single timeline view based on a scheduled time and in association with other multidisciplinary activities for the first patient such that the single timeline view simultaneously presents both the subset of role relevant scheduled activities to be performed for the first patient by the clinician and the one or more multidisciplinary activities to be performed for the first patient by one or more other clinicians; and in response to receiving the user selection of the first patient, removing other patients and the subset of other role relevant scheduled activities associated with the other patients from the timeline view area and simultaneously presenting both the subset of role relevant scheduled activities to be performed for the first patient by the clinician and the one or more multidisciplinary activities to be performed for the first patient by one or more other clinicians within the single timeline view.

2. The one or more computer storage media of claim 1, wherein each role relevant scheduled activity is displayed in the single timeline view using an icon representing a type for the role relevant scheduled activity.

3. The one or more computer storage media of claim 1, wherein each multidisciplinary activity is displayed in the single timeline view using an icon representing a type for the multidisciplinary activity.

4. The one or more computer storage media of claim 1, wherein the method further comprises receiving a user selection of at least one of the multidisciplinary activities; and presenting information regarding the at least one multidisciplinary activity.

5. The one or more computer storage media of claim 4, wherein the information regarding the at least one multidisciplinary activity comprises at least one of an indication of the one or more other clinicians responsible for the multidisciplinary activity, a specific scheduled time for the at least one multidisciplinary activity, and a duration for the at least one multidisciplinary activity.

6. One or more computer storage media, not being a signal per se, having computer-useable instructions embodied thereon for presenting a graphical user interface for facilitating the management of activities for a clinician, the graphical user interface comprising:

a timeline view area presenting role relevant scheduled activities for a plurality of patients assigned to the clinician, wherein the role relevant scheduled activities comprises a subset of role relevant scheduled activities for a first patient and a subset of other role relevant scheduled activities for one or more other patients assigned to the clinician, wherein the subset of role relevant scheduled activities for the first patient comprises one or more activities to be performed by the clinician for a first patient from the plurality of patients, wherein the subset of role relevant scheduled activities for the first patient is presented in a single timeline view based on a scheduled time and in association with other role relevant scheduled activities for the first patient; and wherein the timeline view area simultaneously presents one or more multidisciplinary activities for the first patient within the timeline view area in response to a user selection of the first patient, the one or more multidisciplinary activities comprising activities scheduled to be performed by one or more other clinicians for the first patient, each multidisciplinary activity being presented in the single timeline view based on a scheduled time and in association with other multidisciplinary activities scheduled for the first patient such that the timeline view simultaneously presents both the subset of role relevant scheduled activities to be performed for the first patient by the clinician and the one or more multidisciplinary activities to be performed for the first patient by one or more other clinicians, wherein other patients and the subset of other role relevant scheduled activities associated with the other patients are removed from the timeline view area in response to receiving the user selection of the first patient, and both the subset of role relevant scheduled activities to be performed for the first patient by the clinician and the one or more multidisciplinary activities to be performed for the first patient by one or more other clinicians are simultaneously presented within the single timeline view in response to the user selection.

7. The one or more computer storage media of claim 6, wherein each role relevant scheduled activity is displayed in the single timeline view using an icon representing a type for the role relevant scheduled activity.

8. The one or more computer storage media of claim 6, wherein each multidisciplinary activity is displayed in the single timeline view using an icon representing a type for the multidisciplinary activity.

9. The one or more computer storage media of claim 6, wherein in response to receiving a user selection of at least one of the multidisciplinary activities, information regarding the at least one multidisciplinary activity is presented in the graphical user interface.

10. The one or more computer storage media of claim 9, wherein the information regarding the at least one multidisciplinary activity comprises at least one of an indication of the one or more other clinicians responsible for the multidisciplinary activity, a specific scheduled time for the at least one multidisciplinary activity, and a duration for the at least one multidisciplinary activity.

11. One or more computer storage media, not being a signal per se, storing computer-useable instructions that, when used by one or more computing devices, cause the one or more computing devices to perform a method in a clinical computing environment for facilitating management of activities for a clinician, the method comprising:

presenting a timeline view area having role relevant scheduled activities for a plurality of patients assigned to the clinician, wherein the role relevant scheduled activities comprises a subset of role relevant scheduled activities for a first patient and a subset of other role relevant scheduled activities for one or more other patients assigned to the clinician, wherein the subset of role relevant scheduled activities for the first patient comprises one or more activities to be performed by the clinician for the first patient from the plurality of patients, wherein the subset of role relevant scheduled activities for the first patient is presented in single timeline view based on a scheduled time and in association with other role relevant scheduled activities for the first patient;

upon receiving a first user selection of the first patient, presenting one or more multidisciplinary activities for the first patient within the timeline view area, the one or more multidisciplinary activities comprising activities scheduled to be performed by one or more other clinicians for the first patient, each in the single timeline view based on a scheduled time and in association with other multidisciplinary activities scheduled for the first patient such that the single timeline view simultaneously presents both the subset of role relevant scheduled activities to be performed for the first patient by the clinician and the one or more multidisciplinary activities to be performed for the first patient by one or more other clinicians;

in response to receiving the first user selection of the first patient, removing other patients and the subset of scheduled activities associated with the other patients from the timeline view area such that the timeline view area simultaneously presents the subset of role relevant scheduled activities to be performed for the first patient by the clinician and the one or more multidisciplinary activities to be performed for the first patient by one or more other clinicians;

receiving a second user selection of at least one of the one or more multidisciplinary activities; and upon receiving the second user selection of the at least one multidisciplinary activity, presenting information regarding the selected at least one multidisciplinary activity, the information comprising at least one of an indication of the one or more other clinicians responsible for the at least one multidisciplinary activity, a specific scheduled time for the at least one multidisciplinary activity, and a duration for the at least one multidisciplinary activity.

12. The one or more computer storage media of claim 11, wherein each role relevant scheduled activity is displayed in the single timeline view using an icon representing a type for the role relevant scheduled activity.

13. The one or more computer storage media of claim 11, wherein each multidisciplinary activity is displayed in the single timeline view using an icon representing a type for the multidisciplinary activity.

* * * * *